(12) United States Patent
Madabhushi et al.

(10) Patent No.: US 11,494,900 B2
(45) Date of Patent: Nov. 8, 2022

(54) PROGNOSIS OF PROSTATE CANCER WITH COMPUTERIZED HISTOMORPHOMETRIC FEATURES OF TUMOR MORPHOLOGY FROM ROUTINE HEMATOXYLIN AND EOSIN SLIDES

(71) Applicant: Case Western Reserve University, Cleveland, OH (US)

(72) Inventors: Anant Madabhushi, Shaker Heights, OH (US); Patrick Leo, Honeoye Falls, NY (US); Andrew Janowczyk, East Meadow, NY (US); Kaustav Bera, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 434 days.

(21) Appl. No.: 16/729,697

(22) Filed: Dec. 30, 2019

(65) Prior Publication Data

US 2021/0027459 A1    Jan. 28, 2021

Related U.S. Application Data

(60) Provisional application No. 62/878,894, filed on Jul. 26, 2019.

(51) Int. Cl.
*G06T 7/00*     (2017.01)
*G06T 7/11*     (2017.01)
(Continued)

(52) U.S. Cl.
CPC .......... *G06T 7/0012* (2013.01); *A61B 34/10* (2016.02); *G06K 9/6256* (2013.01);
(Continued)

(58) Field of Classification Search
CPC ............. G06T 7/0012; G06T 7/11; G06T 2207/30081; G06T 2207/30096
See application file for complete search history.

(56) References Cited

U.S. PATENT DOCUMENTS

| | | | |
|---|---|---|---|
| 2006/0110018 A1* | 5/2006 | Chen | G06T 7/0012 382/130 |
| 2010/0027959 A1* | 2/2010 | Obama | H04N 5/772 386/223 |
| 2010/0150417 A1* | 6/2010 | Kshirsagar | G06T 7/0012 382/128 |

OTHER PUBLICATIONS

Lee et al. "Supervised Multi-View Canonical Correlation Analysis (sMVCCA): Integrating Histologic and Proteomic Features for Pretidicting Recurrent Prostate Cancer." IEEE Transactions on Medical Imaging (vol. 34, Issue: 1, Jan. 2015.
(Continued)

*Primary Examiner* — Reginald R Reyes
(74) *Attorney, Agent, or Firm* — Eschweiler & Potashnik, LLC

(57) ABSTRACT

Embodiments facilitate generating a biochemical recurrence (BCR) prognosis by accessing a digitized image of a region of tissue demonstrating prostate cancer (CaP) pathology associated with a patient; generating a set of segmented gland lumen by segmenting a plurality of gland lumen represented in the region of tissue using a deep learning segmentation model; generating a set of post-processed segmented gland lumen; extracting a set of quantitative histomorphometry (QH) features from the digitized image based, at least in part, on the set of post-processed segmented gland lumen; generating a feature vector based on the set of QH features; computing a histotyping risk score based on a weighted sum of the feature vector; generating a classification of the patient as BCR high-risk or BCR low-risk based on the histotyping risk score and a risk score
(Continued)

threshold; generating a BCR prognosis based on the classification; and displaying the BCR prognosis.

27 Claims, 23 Drawing Sheets

(51) Int. Cl.
  *G06K 9/62* (2022.01)
  *G06N 3/08* (2006.01)
  *G16H 70/20* (2018.01)
  *A61B 34/10* (2016.01)

(52) U.S. Cl.
  CPC ............ *G06K 9/6262* (2013.01); *G06N 3/08* (2013.01); *G06T 7/11* (2017.01); *G16H 70/20* (2018.01); *G06T 2207/20081* (2013.01); *G06T 2207/30081* (2013.01); *G06T 2207/30096* (2013.01)

(56) References Cited

OTHER PUBLICATIONS

Lee et al. "Co-Occurring Gland Angularity in Localized Subgraphs: Predicting Biochemical Recurrence in Intermediate-Risk Prostate Cancer Patients." PLOS One, vol. 9, Issue 5, published May 29, 2014.

Leo et al. "Evaluating Stability of Histomorphometric Features Across Scanner and Staining Variations: Prostate Cancer Diagnosis From Whole Slide Images." Journal of Medical Imaging, 3(4), 047502, Oct.-Dec. 2016.

* cited by examiner

| Site | n (n BCR) | Med. BCR (censor) year | Scanner hardware (magnification) |
|---|---|---|---|
| UPenn (Training) | 70 (35) | 1.7 (1.8) | Aperio CS2 (20X) |
| UPenn (Validation) | 350 (114) | 1.7 (2.3) | Aperio ScanScope (40X) |
| UH | 145 (36) | 2.0 (6.6) | 27 on Aperio SCN400 (40X) |
|  |  |  | 36 on Aperio SCN400 (20X) |
|  |  |  | 82 on Zeiss Axio ScanZ1 (40X) |
| TCGA | 175 (7) | 0.5 (1.5) | Unknown, various (40X) |
| WCM | 79 (10) | 1.0 (2.9) | Aperio AT2 (40X) |
| UTurku | 48 (13) | 2.0 (2.5) | 15 on Aperio SCN400 (40X) |
|  |  |  | 33 on Hamamatsu Nanozoomer S60 (20X) |
| MS | 29 (6) | 0.2 (0.4) | Pannoramic 250 FLASH II (40X) |
| Total | 896 (228) | 1.7 (2.2) |  |

Figure 7

|  | Training set | | Validation set | | | | |
| --- | --- | --- | --- | --- | --- | --- | --- |
| Variable | UPenn | UH | UPenn | TCGA | WCM | UTurku | MS |
| Patients | 70 | 145 | 350 | 175 | 79 | 48 | 29 |
| Race | | | | | | | |
| CA | 63 (90.0) | 91 (62.8) | 231 (66.0) | 70 (40.0) | 0 (0.0) | 0 (0.0) | 24 (82.8) |
| AA | 7 (10.0) | 36 (24.8) | 111 (31.7) | 3 (1.7) | 79 (100.0) | 0 (0.0) | 2 (6.9) |
| Other | 0 (0.0) | 5 (3.4) | 8 (2.3) | 1 (0.6) | 0 (0.0) | 48 (100.0) | 1 (3.4) |
| Unknown | 0 (0.0) | 13 (9.0) | 0 (0.0) | 101 (57.7) | 0 (0.0) | 0 (0.0) | 2 (6.9) |
| Patient age, years (median [Q1, Q3]) | 59 (55, 65) | 61 (57, 64) | 61 (56, 66) | 60 (55, 65) | 61 (56, 66) | 65 (61, 68) | 63 (58, 67) |
| Unknown | 0 | 130 | 0 | 0 | 0 | 24 | 0 |
| pT stage | | | | | | | |
| 1 | 0 (0.0) | 0 (0.0) | 0 (0.0) | 0 (0.0) | 0 (0.0) | 1 (2.1) | 0 (0.0) |
| 2 | 36 (51.4) | 9 (6.2) | 163 (46.6) | 90 (51.4) | 63 (79.7) | 28 (58.3) | 16 (55.2) |
| 3 | 34 (48.6) | 9 (6.2) | 187 (53.4) | 80 (45.7) | 16 (20.3) | 18 (37.5) | 13 (44.8) |
| 4 | 0 (0.0) | 0 (0.0) | 0 (0.0) | 2 (1.1) | 0 (0.0) | 0 (0.0) | 0 (0.0) |
| Unknown | 0 (0.0) | 127 (87.6) | 0 (0.0) | 3 (1.7) | 0 (0.0) | 1 (2.1) | 0 (0.0) |
| Pre-operative PSA, ng/mL (median [Q1, Q3]) | 8 (5, 11) | 6 (5, 8) | 6 (5, 9) | 6 (5, 9) | 6 (4, 8) | 8 (6, 10) | 8 (5, 13) |
| Unknown | 0 | 67 | 4 | 5 | 3 | 1 | 0 |
| RP Gleason grade group [23] | | | | | | | |
| 1 | 8 (11.4) | 33 (22.8) | 74 (21.1) | 20 (11.4) | 17 (21.5) | 9 (18.8) | 1 (3.4) |
| 2 | 38 (54.3) | 81 (55.9) | 163 (46.6) | 73 (41.7) | 40 (50.6) | 17 (35.4) | 15 (51.7) |
| 3 | 16 (22.9) | 11 (7.6) | 68 (19.4) | 43 (24.6) | 15 (19.0) | 8 (16.7) | 8 (27.6) |
| 4 | 4 (5.7) | 2 (1.4) | 21 (6.0) | 23 (13.1) | 1 (1.3) | 4 (8.3) | 0 (0.0) |
| 5 | 4 (5.7) | 4 (2.8) | 22 (6.3) | 16 (9.1) | 6 (7.6) | 9 (18.8) | 5 (17.2) |
| Unknown | 0 (0.0) | 14 (9.7) | 2 (0.6) | 0 (0.0) | 0 (0.0) | 1 (2.1) | 0 (0.0) |
| Positive surgical margins, No. (%) | 30 (42.9) | 9 (6.2) | 207 (59.1) | 29 (16.6) | 8 (10.1) | 7 (14.6) | 1 (3.4) |
| Unknown | 0 (0.0) | 130 (89.7) | 1 (0.3) | 16 (9.1) | 0 (0.0) | 1 (2.1) | 0 (0.0) |
| Seminal vesicle invasion, No. (%) | 11 (15.7) | 2 (1.4) | 47 (13.4) | 0 (0.0) | 0 (0.0) | 0 (0.0) | 7 (24.1) |
| Unknown | 0 (0.0) | 131 (90.3) | 0 (0.0) | 175 (100.0) | 79 (100.0) | 48 (100.0) | 0 (0.0) |
| Extraprostatic invasion, No. (%) | 34 (48.6) | 7 (4.8) | 168 (48.0) | 0 (0.0) | 0 (0.0) | 4 (8.3) | 11 (37.9) |
| Unknown | 0 (0.0) | 131 (90.3) | 0 (0.0) | 175 (100.0) | 79 (100.0) | 41 (85.4) | 0 (0.0) |
| Follow-up of censored patients, years (median [Q1, Q3]) | 2 (1, 4) | 7 (5, 9) | 2 (2, 5) | 1 (1, 3) | 2 (0, 4) | 2 (2, 4) | 0 (0, 1) |
| Patients with BCR, No. (%) | 35 (50.0) | 45 (31.0) | 114 (32.6) | 7 (4.0) | 10 (12.7) | 11 (22.9) | 6 (20.7) |

Figure 8

| Feature name | Hazard ratio |
|---|---|
| Shape: Mean invariant moment 2 | 0.97 |
| Shape: Mean Fourier descriptor 4 | 1.02 |
| Shape: Standard deviation of smoothness | 0.97 |
| Shape: Median distance ratio | 0.93 |
| Shape: 5% / 95% perimeter ratio | 1.00 |
| Shape: 5% / 95% Fourier descriptor 1 | 1.02 |
| Shape: 5% / 95% Fourier descriptor 6 | 0.99 |
| Sub-Graph: Skewness of edge length | 1.04 |
| Haralick: Mean correlation | 0.96 |

Figure 12

| Variable | UVA Hazard ratio (95% CI) | p | MVA (Histotyping continuous) Hazard ratio (95% CI) | p | MVA (Histotyping categorical) Hazard ratio (95% CI) | p |
|---|---|---|---|---|---|---|
| Histotyping (increase of 0.1) | 1.45 (1.26 - 1.67) | <.001 | 1.33 (1.14 - 1.54) | <.001 | -- | -- |
| Histotyping low-risk | ref | 1 | -- | -- | ref | 1 |
| Histotyping high-risk | 2.38 (1.72 - 3.30) | <.001 | -- | -- | 2.37 (1.69 - 3.33) | <.001 |
| Gleason grade group 1 | ref | 1 | ref | 1 | ref | 1 |
| Gleason grade group 2 | 1.22 (0.71 - 2.11) | 0.476 | 0.84 (0.48 - 1.47) | 0.545 | 0.78 (0.45 - 1.38) | 0.396 |
| Gleason grade group 3 | 2.88 (1.65 - 5.02) | <.001 | 1.71 (0.95 - 3.06) | 0.073 | 1.77 (0.99 - 3.15) | 0.055 |
| Gleason grade group 4 | 3.46 (1.76 - 6.81) | <.001 | 2.90 (1.45 - 5.82) | 0.003 | 2.96 (1.48 - 5.93) | 0.002 |
| Gleason grade group 5 | 5.36 (2.94 - 9.78) | <.001 | 2.47 (1.31 - 4.66) | 0.005 | 2.54 (1.36 - 4.75) | 0.003 |
| Positive surgical margins | 2.69 (1.90 - 3.79) | <.001 | 2.12 (1.48 - 3.06) | <.001 | 2.28 (1.58 - 3.28) | <.001 |
| Log2 preoperative PSA, ng/mL | 1.78 (1.50 - 2.12) | <.001 | 1.63 (1.36 - 1.95) | <.001 | 1.65 (1.38 - 1.98) | <.001 |
| Stage <T2b | ref | 1 | ref | 1 | ref | 1 |
| Stage ≥T2b | 2.22 (1.38 - 3.58) | <.001 | 1.19 (0.71 - 1.99) | 0.521 | 1.19 (0.71 - 2.00) | 0.510 |

Figure 14

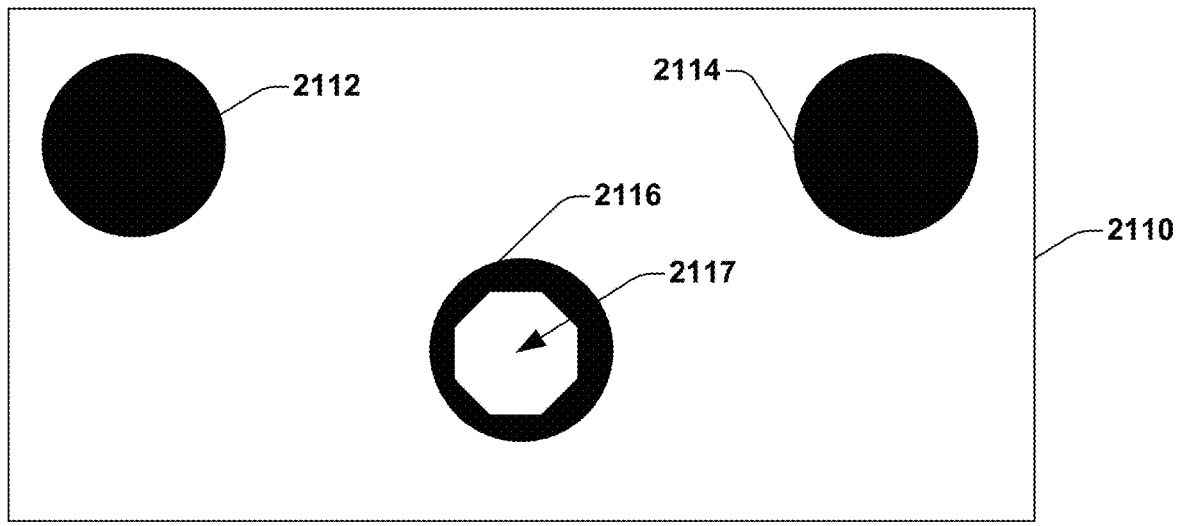
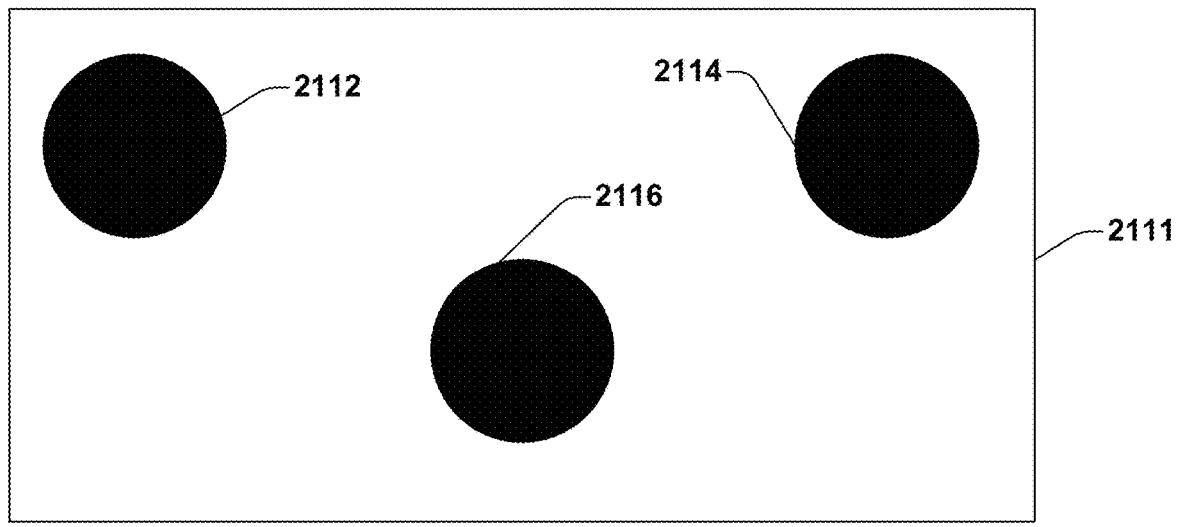
Figure 21

PROGNOSIS OF PROSTATE CANCER WITH COMPUTERIZED HISTOMORPHOMETRIC FEATURES OF TUMOR MORPHOLOGY FROM ROUTINE HEMATOXYLIN AND EOSIN SLIDES

CROSS REFERENCE TO RELATED APPLICATIONS

This application claims the benefit of U.S. Provisional Patent Application No. 62/878,894 filed Jul. 26, 2019, the contents of which are herein incorporated by reference in their entirety.

FEDERAL FUNDING NOTICE

This invention was made with government support under the grants CA199374, CA202752, CA208236, CA216579, CA220581, RR012463, CA239055, and EB028736 awarded by the National Institutes of Health; grant IBX004121A awarded by the United States Depart-ment of Veterans Affairs; grants W81XWH-19-I-0668, W81XWH-15-I-0558, W81XWH-18-1-0440, and W81XWH-16-1-0329 awarded by the United States Depart-ment of Defense; and grant DGE1451075 awarded by the National Science Foundation. The government has certain rights in the invention.

BACKGROUND

One curative treatment for prostate cancer (CaP) is radical prostatectomy (RP). RP is the surgical removal of the entire prostate. Following RP, some patients will experience the return of cancer, known as biochemical recurrence (BCR). BCR may be detected by two consecutive serum prostate-specific antigen (PSA) test results >0.2 ng/mL. BCR is a surrogate endpoint for CaP, carrying a hazard ratio (HR) of 4.32 for disease-specific death. Adjuvant therapy reduces the risk of metastasis and disease-specific death, although adjuvant therapy is not appropriate for all patients due to the low overall mortality rate of CaP. If a patient's future BCR status could be known at the time of RP surgery, high-risk patients could begin adjuvant therapy sooner with the goal of avoiding metastasis, while low-risk patients could be spared the morbidity associated with further treatment.

Existing BCR prognostic tools, including nomograms, produce a risk score based on several clinical variables, but require human observers for Gleason grading. Existing approaches thus suffer from intra-observer and inter-observer variations. In addition to nomograms, some existing BCR prognosis approaches employ molecular companion diagnostics for outcome prognosis. However, these existing approaches are tissue destructive, expensive, and their results are only available after a significant delay, which may postpone treatment. Furthermore, existing CaP diagnostic tools are exclusively prognostic, rather than predictive of benefit of therapy, and none provide perfect risk stratification. Thus, existing approaches to BCR prognosis or predicting benefit of therapy in CaP are sub-optimal.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 7 illustrates a table of cohort data and scanner hardware associated with exemplary training cohorts.

FIG. 8 illustrates a table of clinical data associated with exemplary training cohorts.

FIG. 12 illustrates a table of exemplary quantitative histomorphometry (QH) features according to various embodiments discussed herein.

FIG. 14 illustrates Cox proportional hazard univariable (VA) and multivariable analysis of BCR on a validation set.

FIG. 21 illustrates an example set of segmented gland lumen.

DETAILED DESCRIPTION

Figure 1:
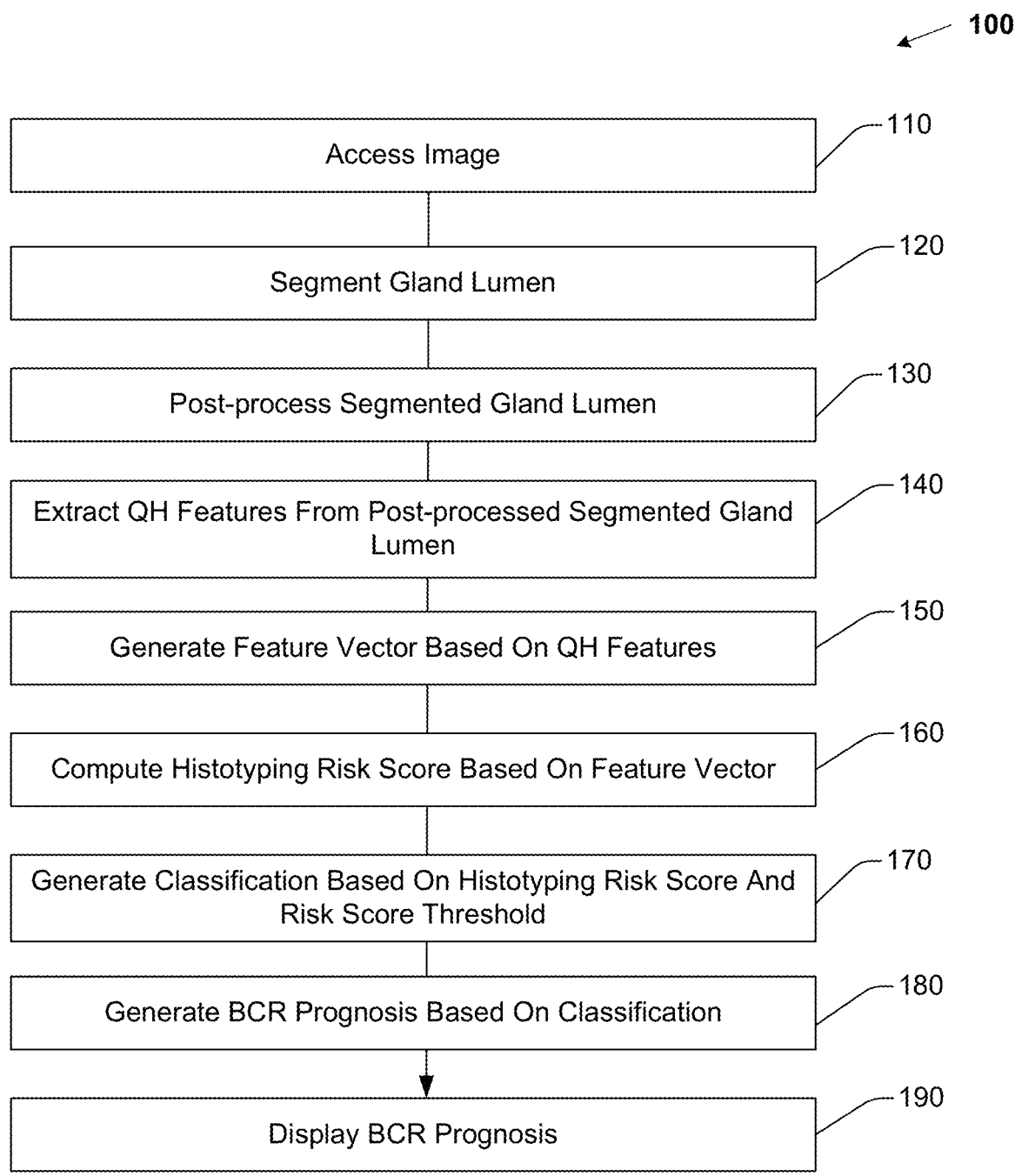
FIG. 1 illustrates a workflow diagram of an example method or set of operations according to various embodiments discussed herein.

Quantitative histomorphometry (QH) is the automated analysis of digitized pathology tissue imagery through feature mining and machine learning. QH may analyze primitives represented in digitized pathology tissue imagery, including, for example, gland lumens, nuclei, and image texture, to calculate features which quantitatively characterize tissue morphology. These features may then be correlated with disease behaviour through machine learning models for diagnosis or outcome prognosis. However, some existing approaches rely on black-box features that do not clearly map to tumor morphology, which limits their clinical adoption. Additionally, there is an absence of validation of existing QH techniques on large multi-site cohorts, due to the pre-analytic variability between sites in, for example, sample preparation.

Embodiments include operations, methods, apparatus, and other embodiments that facilitate rapid, objective risk assessment to identify patients who are likely to have adverse outcomes after primary treatment for CaP. Embodiments facilitate automated assessment of tissue or glandular morphology to generate a prediction of BCR risk following RP. Embodiments may identify specific quantitative measures associated with aggressive CaP to characterize high-risk disease. Embodiments include generation of a predictive model robust to sample preparation variation, including sample preparation variation across different institutions. Embodiment may validate the predictive model on an independent validation set. Embodiments account for inter-site differences in sample preparation to facilitate generation of a predictive model that generalizes across imagery associated with patients acquired across multiple, different institutions. Embodiments further add value over existing risk assessment methods, especially in low-risk patients. Embodiments generate a BCR prognosis using automated analysis of a digitized hematoxylin and eosin (H&E) stained slide of a region of tissue demonstrating CaP associated with a patient. Embodiments may generate a BCR prognosis further based on clinical values associated with a patient. A prognosis, including a BCR prognosis, may include, for example, a survival range. Embodiments may optionally further generate a metastasis prognosis.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Various embodiments can employ techniques discussed herein to facilitate generating a prognosis of BCR associated with a patient, or generating a classification of the patient as low-risk of BCR or as high-risk of BCR in CaP. FIG. 1 illustrates a flow diagram of an example method or set of operations 100 that facilitates generating a prognosis associated with a patient demonstrating CaP according to various embodiments discussed herein. The prognosis may be a BCR prognosis. Operations 100 may further facilitate generation of a classification of a patient demonstrating CaP as BCR high-risk or BCR low-risk according to various embodiments discussed herein. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations or methods described herein. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

Operations 100 includes, at 110, accessing a digitized image of a region of tissue demonstrating prostate cancer (CaP) pathology. The region of tissue includes a tumor region. The region of tissue may include gland lumen represented in the digitized image. The digitized image includes a plurality of pixels, a pixel having an intensity. The digitized image is associated with a patient. In one embodiment, the image is a digitized image of an H&E stained slide of a region of tissue demonstrating CaP. In one embodiment, the image includes an annotated tumor region. In one embodiment, the digitized image is acquired at 10× magnification, with a resolution of 1 micron per pixel. In one embodiment, accessing the digitized image may include downsizing the digitized image. For example, in one embodiment, the digitized image may be downsized to 10× magnification with a resolution of 1 micron per pixel from 20× magnification with a resolution of 0.5 microns per pixel. In one embodiment, the digitized image may be downsized to 10× magnification with a resolution of 1 micron per pixel from 40× magnification with a resolution of 0.25 microns per pixel. The accessed digitized image, for example, a digitized H&E stained slide, can be stored in memory locally or remotely, and can be obtained via a medical imaging device one of concurrently with method or operations 100 (for example, via a medical imaging device implementing method or operations 100) or prior to method or operations 100, or other operations described herein. Accessing the digitized image, for example, the digitized H&E stained slide image, includes acquiring electronic data, reading from a computer file, receiving a computer file, reading from a computer memory, or other computerized activity not practically performed in the human mind.

Operations 100 also includes, at 120, generating a set of segmented gland lumen by segmenting a plurality of gland lumen represented in the tumor region using a deep learning segmentation model. In one embodiment, segmenting a gland lumen using a deep learning segmentation model includes segmenting a gland lumen using a deep learning model trained to segment gland lumen represented in a digitized hematoxylin and eosin (H&E) stained image of a region of tissue demonstrating CaP. A segmented gland lumen may comprise a boundary. Embodiments may further include training the deep learning segmentation model according to various techniques described herein. In one embodiment, the deep learning segmentation model is a modified UNet deep learning model. Generating the set of segmented gland lumen includes acquiring electronic data, reading from a computer file, receiving a computer file, reading from a computer memory, or other computerized activity not practically performed in the human mind.

Figure 4:
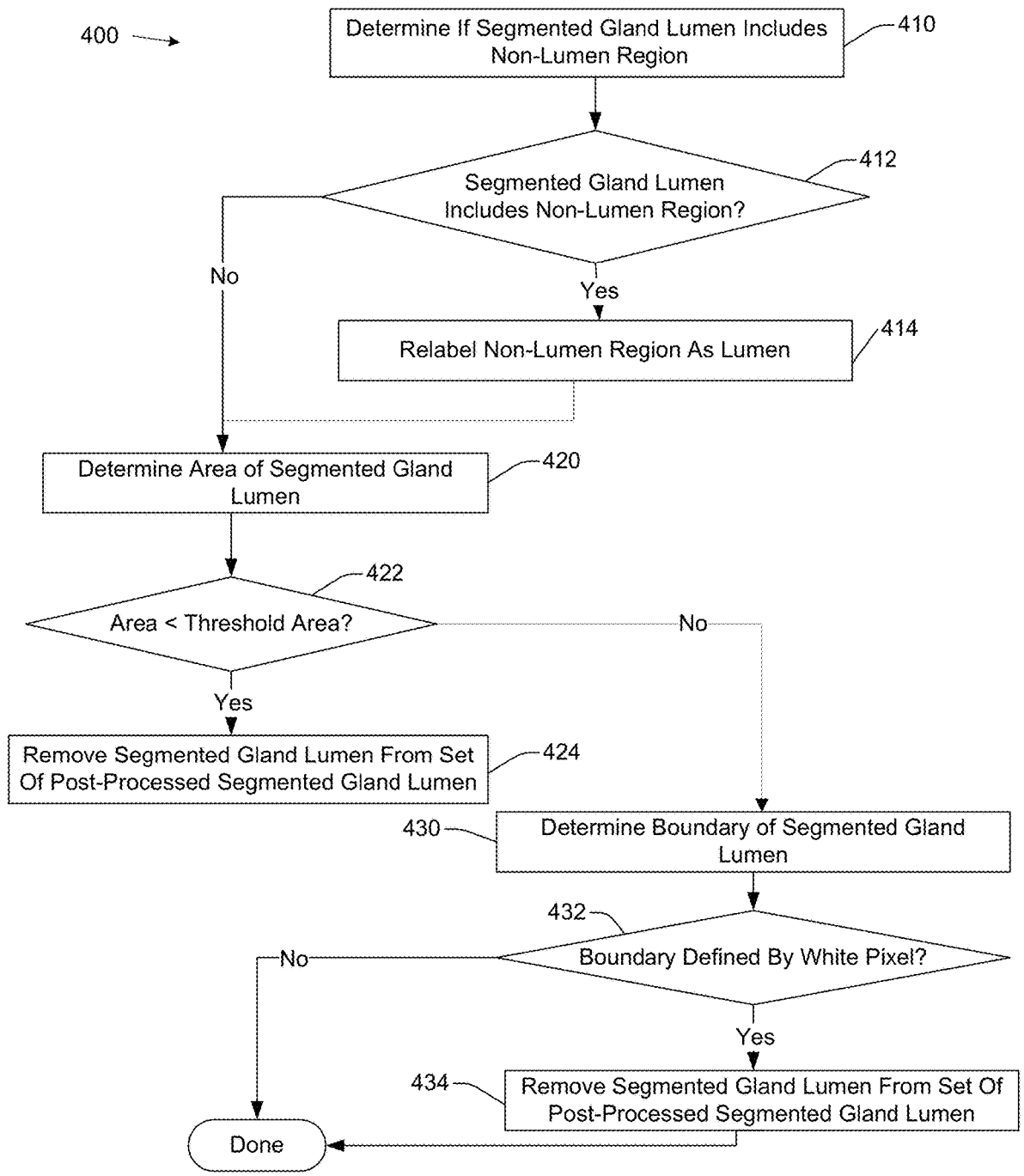
FIG. 4 illustrates a workflow diagram of an example method or set of operations according to various embodiments discussed herein.

Operations 100 also includes, at 130, generating a set of post-processed segmented gland lumen by post-processing the set of segmented gland lumen. The presence of artifacts in digitized H&E stained images is a problem in the segmentation of gland lumen and the extraction of features, including QH features, from segmented gland lumen represented in digitized H&E stained images. Embodiments facilitate improved segmentation of gland lumen and improved extraction of QH features by post-processing the set of segmented gland lumen. In one embodiment, generating the post-processed set of segmented gland lumen by post-processing the set of segmented gland lumen includes defining a set of post-processed segmented gland lumen, where the set of post-processed segmented gland lumen includes the members of the set of segmented gland lumen. For example, in one embodiment, an initial post-processed set of segmented gland lumen may include all the members of the set of segmented gland lumen. Embodiments may correct, re-label, or remove objects incorrectly labelled as segmented gland lumen from the initial post-processed set of segmented gland lumen according to techniques described herein. For example, embodiments may detect incorrectly labelled segmented gland lumen and re-label objects incorrectly labelled as gland lumen. Embodiments may further determine properties associated with a member of set of post-processed segmented gland lumen, and remove the member from the set of post-processed segmented gland lumen upon determining that the member of the set of post-processed segmented gland lumen has, for example, an area less than a threshold area, or has boundary defined by more than a threshold level of white pixels. Generating the set of post-processed segmented gland lumen includes acquiring electronic data, reading from a computer file, receiving a computer file, reading from a computer memory, or other computerized activity not practically performed in the human mind. FIG. 4 illustrates an example set of operations 400 for generating the set of post-processed segmented gland lumen. Operations 400 for generating the set of post-processed segmented gland lumen may be employed by embodiments described herein, including for example, operations 100, 200, 300, 600, 2000, 2200, or apparatus 1700 or 1800.

Operations 400 includes, at 410, determining if a member of the set of post-processed segmented gland lumen includes a non-lumen region. For example, a segmented gland lumen may include an area that has been incorrectly classified as non-gland lumen by the deep learning segmentation model. For example, the lumen segmentation model or deep learning segmentation model trained to segment gland lumen may have created a doughnut-shaped segmentation, which is unlikely to be an accurate representation of a gland lumen since it is unlikely that a lumen has non-lumen in the middle surrounded by lumen. FIG. 21 illustrates an example set of segmented gland lumen 2110. Example set of gland lumen 2110 includes segmented gland lumen 2112, 2114, and 2116. Segmented gland lumen 2116 includes an area 2117 that has been incorrectly classified as non-gland lumen. For example, segmented gland lumen 2116 includes a hole indicated by area 2117.

Returning to FIG. 4, upon determining at 412 that the member of the set of post-processed segmented gland lumen includes a non-lumen region, operations 400 includes, at 414, relabeling the non-lumen region as lumen. FIG. 21 further illustrates an example set of post-processed segmented gland lumen 2111. Example set of post-processed segmented gland lumen 2111 is similar to the example set of segmented gland lumen 2110, and includes segmented gland lumen 2112, 2114, and 2116. Note that area 2117 has been removed from segmented gland lumen 2116 in the set of post-processed segmented gland lumen 2111.

Returning to FIG. 4, upon determining at 412 that the member of the set of post-processed segmented gland lumen does not include a non-lumen region, operations 400 includes, at 420, determining an area of the member of the set of segmented gland lumen. In one embodiment, the area is measured in $\mu m^2$, while in another embodiment, the area may be measured in other units, for example, pixels.

Upon determining at 422 that the member of the set of segmented gland lumen has an area less than a threshold area, operations 400 also includes, at 424, removing the member of the set of segmented gland lumen from the set of post-processed segmented gland lumen. In one embodiment, the threshold area is 4 $\mu m^2$. In another embodiment, the threshold area may have another, different value, for example, 3 $\mu m^2$, or 5 $\mu m^2$, or other value. Removing objects incorrectly labeled as gland lumen, identified by their having an area less than the threshold area, improves the performance of embodiments, including systems, apparatus, or computers in which embodiments are implemented, by excluding non-lumen objects from analysis of lumen morphology. Excluding non-lumen objects from analysis of lumen morphology according to techniques described herein may have the practical effects of reducing computing resources used by systems, apparatus, or computers in which embodiments are implemented, and improving the accuracy of systems, apparatus, or computers in which embodiments are implemented.

Upon determining at 422 that the member of the set of segmented gland lumen has an area greater than or equal to the threshold area, operations 400 includes, at 430, determining a boundary of a member of the set of segmented gland lumen. Embodiments may determine the boundary by dilating the segmented object, for example, the member of the set of segmented gland lumen, and subtracting the original object mask from the dilated mask. In this embodiment, the segmented object is dilated by a disk-shaped structuring elements with a radius of 1 pixel. In another embodiment, another, different radius may be employed.

Upon determining, at 432, that the boundary of the member of the set of segmented gland lumen is defined by a white pixel, operations 400 includes, at 434, removing the segmented gland lumen from the set of post-processed segmented gland lumen. In this embodiment, a white pixel may be defined by the pixel's intensity being greater than a threshold. In this embodiment the intensity threshold is a unit-less number having a value of two-hundred and twenty (220). In this example, the intensity threshold having a value of two-hundred and twenty (220) is applicable where the digitized image is represented in a format in which pixel intensity takes on a value between 0 and 255. In another embodiment, the intensity threshold may have another, different value. In another embodiment, the intensity threshold may be represented as a percentage of a maximum threshold, for example, 80%, 86%, or 90%, or as a fraction of a maximum threshold. In one embodiment, determining that the boundary of the member of the set of segmented gland lumen is defined by a white pixel includes dilating the boundary of the segmented gland lumen by 1 pixel, and determining if the dilated boundary includes more than 5% white pixels. In another embodiment, determining that the boundary of the member of the set of segmented gland lumen is defined by a white pixel includes dilating the boundary of the segmented gland lumen by 1 pixel, and determining if the dilated boundary includes more than another, different percentage of white pixels, for example, 3%, or 7%, or other percentage.

Returning to FIG. 1, operations 100 also includes, at 140, extracting a set of quantitative histomorphometry (QH) features from the digitized image based, at least in part, on the set of post-processed segmented gland lumen. In one embodiment, the members of the set of QH features may be selected based on stability filtering, or Cox regression modelling with elastic net regularization, from digitized H&E stained slides acquired across multiple institutions as described herein. By selecting the set of QH features based on stability filtering, or Cox regression modelling with elastic net regularization, from digitized H&E stained slides acquired across multiple institutions, embodiments facilitate generating a prognosis that accounts for inter-site differences in sample preparation. In another embodiment, the members of the set of QH features may be selected using other techniques, including, for example, correlation filtering, Cox regression with LASSO penalization, Cox regression with ridge penalization, or logistic regression. Extracting the set of QH features includes acquiring electronic data, reading from a computer file, receiving a computer file, reading from a computer memory, or other computerized activity not practically performed in the human mind.

In one embodiment, the set of QH features includes at least nine features. In this embodiment, the set of QH features includes a set of gland lumen features, a set of sub-graph features, and a set of texture features. In this embodiment, the set of gland lumen features is based, at least in part, on the post-processed set of segmented gland lumen. In this embodiment, the set of texture features includes at least one texture feature extracted from the tumor region. In this embodiment, the set of sub-graph features includes at least one sub-graph feature extracted from the tumor region. In one embodiment, the set of QH features includes at least seven gland lumen shape features, at least one sub-graph feature, and at least one texture feature. In one embodiment, the set of QH features includes a mean invariant moment 2 feature, a mean Fourier descriptor 4 feature, a standard deviation of smoothness feature, a median distance ratio feature, a $5^{th}$ percentile/$95^{th}$ percentile perimeter ratio feature, a $5^{th}$ percentile/$95^{th}$ percentile Fourier descriptor 1 feature, a $5^{th}$ percentile/$95^{th}$ percentile Fourier descriptor 6 feature, a skewness of edge length sub-graph feature, and a Haralick mean correlation feature. In another embodiment, another, different number of QH features may be extracted, or the set of QH features may include other, different QH features.

In one embodiment, extracting the set of QH features includes extracting 216 gland lumen features. In this embodiment, 26 Haralick texture features are extracted from the entire tumor region. In another embodiment, another, different number of gland lumen features may be extracted, or another, different number of Haralick texture features may be extracted.

Operations 100 also includes, at 150, generating a feature vector based on the set of QH features. In one embodiment, a 242 element feature vector is generated based on 216 extracted gland lumen features and 26 extracted Haralick features, extracted from the set of post-processed gland lumen and the tumor region represented in the digitized H&E stained image. In another embodiment, the feature vector may include another, different number of elements. For example, when the set of QH features includes nine (9) QH features, the feature vector may have nine elements. In another embodiment, generating the feature vector based on the set of QH features may include generating a feature vector having the same cardinality as the set of QH features.

Embodiments may normalize the feature vector by normalizing the set of QH features that comprise the feature vector. In one embodiment, normalizing the set of QH features includes subtracting the 242 element vector of the training set feature mean values from the feature vectors from each image, followed by element-wise division of the digitized H&E stained image's feature vector by the 242 element training set feature standard deviation values. In another embodiment, other normalization techniques may be employed.

Operations 100 also includes, at 160, computing a histotyping risk score based on a weighted sum of the feature vector. In one embodiment computing the histotyping risk score includes multiplying a normalized feature vector by a vector of β values. The vector of β values may be obtained from a histotyping model trained according to techniques described herein. In this embodiment, computing the histotyping risk score further includes computing the sum of the products of the normalized feature vectors and their corresponding β values. In one embodiment, all but nine elements of the β vector, corresponding to the features included in the trained model, are zero. In this example, the nine elements of the β vector, corresponding to the features included in the trained model correspond to the set of QH features extracted at 140. In one embodiment, the computed histotyping risk score has a value within the range [−0.72, 0.46]. In this embodiment, a higher value, for example, 0.4 is associated with an increased risk of BCR, while a lower value, for example, −0.5, is associated with a lower risk of BCR. In another embodiment, the histotyping risk score may have a value within another, different range, for example, [−1, 1], or other range. In another embodiment, all but another, different number of elements of the β vector, for example, five or fifteen, corresponding to five or fifteen features included in the trained model respectively, are zero. In embodiments described herein, the vector of β values can be obtained one of concurrently with method or operations 100 (for example, via a system, apparatus, computer, or medical imaging device implementing method or operations 100) or prior to method or operations 100, or other operations described herein. In another embodiment, the feature vector is non-normalized, and computing the histotyping risk score includes multiplying the non-normalized feature vector by the vector of β values. Computing the histotyping risk score includes acquiring electronic data, reading from a computer file, receiving a computer file, reading from a computer memory, or other computerized activity not practically performed in the human mind.

Operations 100 also includes, at 170, generating a classification of the patient as BCR high-risk or BCR low-risk based on the histotyping risk score and a risk score threshold. In one embodiment, generating the classification includes applying a risk score threshold identified on the training set to the histotyping risk score computed at 160 to stratify or categorize the patient as BCR low-risk or BCR high-risk according to whether the image risk score is less than (<) the risk score threshold value, or greater than or equal to (>=) the risk score threshold value. In one embodiment, the risk score threshold has a value of 0.0960. In another embodiment, the risk score threshold may have another, different value. The risk score threshold may be determined based, at least in part, on a range selected from within the range the histotyping risk score is obtained, for example, [−0.72, 0.46], [−1, 1], or other, different range. The risk score threshold may be computed according to various techniques described herein.

For example, in one embodiment, the risk score threshold is computed based on midpoints between the histotyping risk score of each training set patient. In this embodiment, risk score thresholds which yielded a group smaller than one-third of the training set or a logrank p-value >0.05 are discarded. Next, embodiments may identify the set of risk score thresholds which yielded the maximum absolute difference in median survival time between the groups. From among identified risk score thresholds, the risk score threshold with the largest hazard ratio is selected and applied to the training and validation sets to create Histotyping stratifications. Histotyping stratifications may include, for example, BCR low-risk, or BCR high-risk. In another embodiment, histotyping stratifications may include, other, different clinical endpoints associated with the patient, for example, metastasis high-risk or metastasis low-risk.

Figure 23:
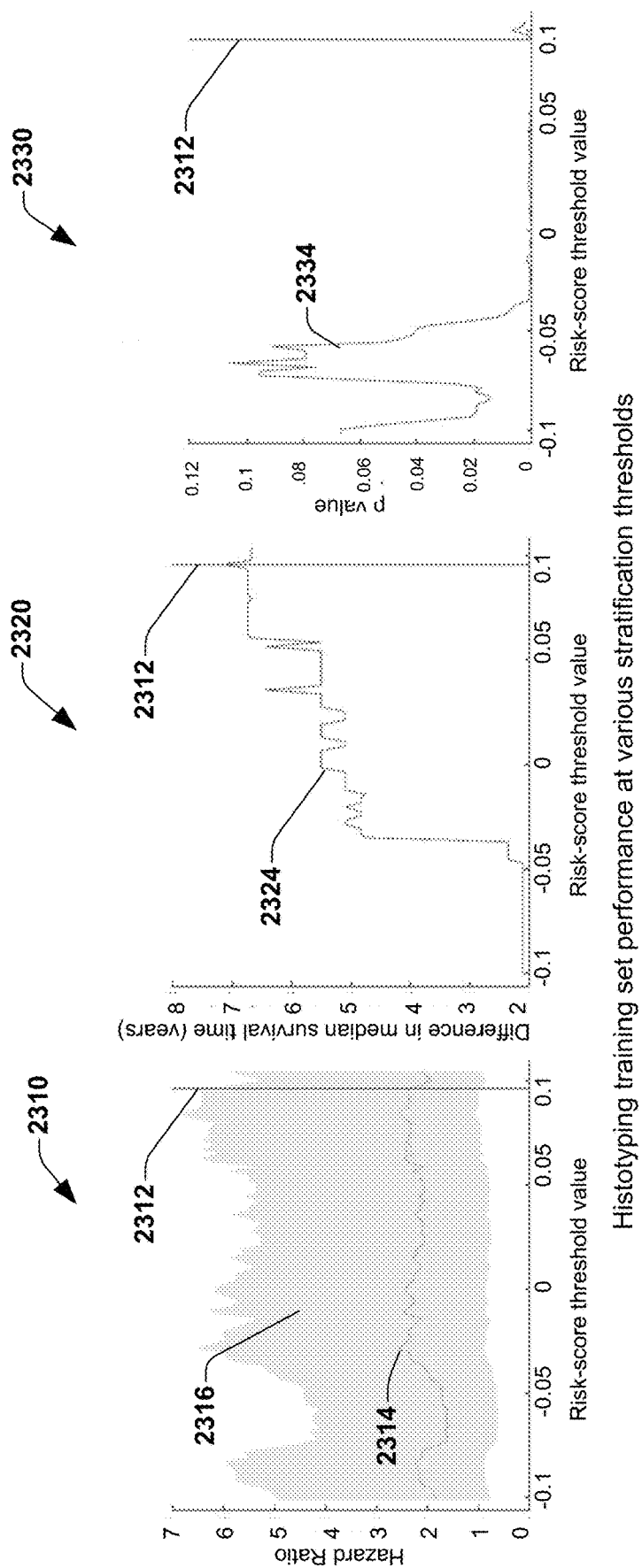
FIG. 23 illustrates an example risk score threshold value according to various embodiments discussed herein.

FIG. 23 illustrates an example risk score threshold value determined according to various techniques described herein. FIG. 23 illustrates, at 2310, Histotyping hazard ratio 2314 and 95% confidence interval 2316. FIG. 23 also illustrates, at 2320, difference in median survival time 2324. FIG. 23 further illustrates, at 2330, the logrank p-value 2334 in the training set at various stratification thresholds. The risk score threshold value used in this example is marked by a vertical line 2312.

In another embodiment, other classification schemes may be employed. For example, in one embodiment, the patient may be classified histotyping low-risk, histotyping high-risk, or histotyping indeterminate risk. In another embodiment, the patient may be classified BCR low-risk, BCR high-risk, or BCR indeterminate risk. In one embodiment, where the patient is classified BCR low-risk or BCR high-risk, the classification is generated with at least: p<0.0001, HR=2.27, 95% confidence interval: 1.59-3.26, and concordance index=0.66. In another embodiment, the patient may be classified as metastasis high-risk or metastasis low-risk. Generating the classification includes acquiring electronic data, reading from a computer file, receiving a computer file, reading from a computer memory, or other computerized activity not practically performed in the human mind.

Operations 100 also includes, at 180, generating a BCR prognosis based, at least in part, on the classification. Generating the BCR prognosis may include, for example, generating a prognosis that the patient is likely to experience BCR, where the patient is classified as BCR high-risk, or generating a prognosis that the patient is unlikely to experience BCR, where the patient is classified as BCR low-risk. In one embodiment, the BCR prognosis is prognostic of BCR with: p<0.0001, HR=2.27, 95% confidence interval: 1.59-3.26, and concordance index=0.66. In another embodiment, a metastasis prognosis may be generated based on the classification. For example, embodiments may generate a prognosis that the patient is likely to experience metastasis, where the patient is classified as metastasis high-risk, or generating a prognosis that the patient is unlikely to experience metastasis, where the patient is classified as metastasis low-risk. Generating the BCR prognosis includes acquiring electronic data, reading from a computer file, receiving a computer file, reading from a computer memory, or other computerized activity not practically performed in the human mind.

Operations 100 further includes, at 190, displaying the BCR prognosis. In one embodiment, the set of operations 100 further includes, at 190, displaying the BCR prognosis and optionally displaying one or more of the classification, the digitized image, the H&E stained image, or the histotyping risk score. Displaying the BCR prognosis, and optionally displaying one or more of the classification, the digitized image, the H&E stained image, or the histotyping risk score may include displaying the BCR prognosis and optionally displaying one or more of the classification, the digitized image, the H&E stained image, or the histotyping risk score on a computer monitor, a smartphone display, a tablet display, or other displays. Displaying the BCR prognosis, and optionally displaying one or more of the classification, the digitized image, the H&E stained image, or the histotyping risk score can also include printing the BCR prognosis, and optionally printing one or more of the classification, the digitized image, the H&E stained image, or the histotyping risk score. Displaying the BCR prognosis and optionally displaying one or more of the classification, the digitized image, the H&E stained image, or the histotyping risk score can also include controlling a CaP BCR prediction system, a personalized medicine system, a medical imaging system, a monitor, or other display, to display operating parameters or characteristics of a machine learning classifier, including a deep learning classifier or deep learning model, during at least one of training and testing of the machine learning classifier, or during clinical operation of the machine learning classifier. For example, embodiments may display operating parameters of a machine learning classifier or deep learning model employed in operations 100, 200, 300, 400, 500, 600, 2000, or 2200, for example, a lumen segmentation model or deep learning model trained to segment gland lumen.

By displaying the BCR prognosis and optionally displaying one or more of the classification, the digitized image, the H&E stained image, or the histotyping risk score, example embodiments provide a timely and intuitive way for a human medical practitioner to more accurately predict treatment response, to more accurately stratify or classify an ROI or the patient associated with the ROI into a treatment response category (e.g., high-risk of BCR, low risk of BCR), or generate a prognosis for the patient associated with the ROI, thus improving on existing approaches to predicting BCR or generating a prognosis in CaP. By displaying the BCR prognosis and optionally displaying one or more of the classification, the H&E stained image, or the histotyping risk score, example embodiments may further provide a timely and intuitive way for a human medical practitioner to more accurately identify CaP patients at high-risk of BCR, and to improve treatment management accordingly. Embodiments may further display a metastasis prognosis computed according to techniques described herein.

Figure 2:
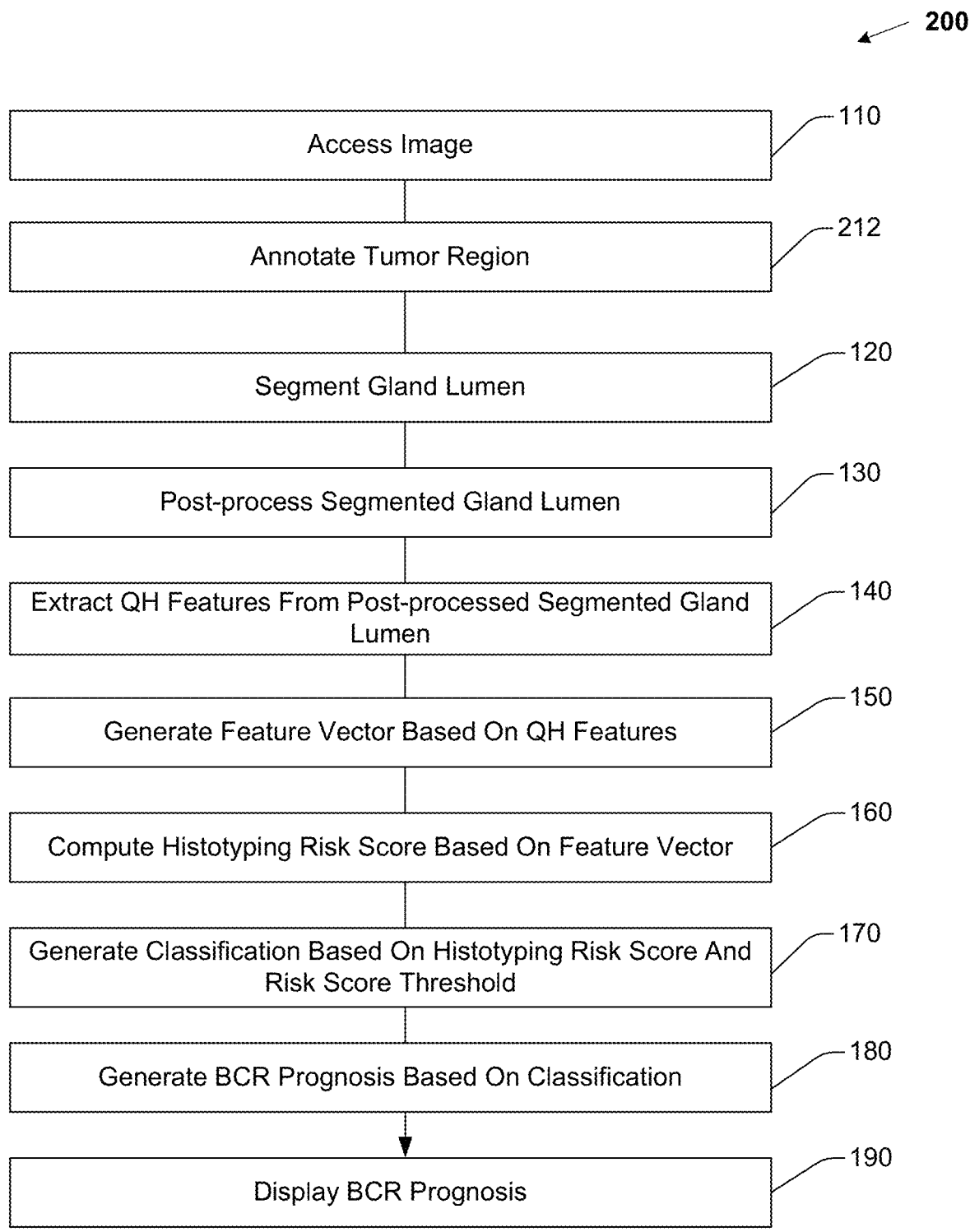
FIG. 2 illustrates a workflow diagram of an example method or set of operations according to various embodiments discussed herein.

FIG. 2 illustrates a set of operations 200 that is similar to operations 100, but that includes additional elements and details. Operations 200 includes operations 110-190, but also includes, at 212, annotating the tumor region represented in the image. In one embodiment, the tumor region may be automatically annotated using, for example, neural networks, QH techniques, or analysis of immunohistochemically stained consecutive slices of tissue. In various embodiments described herein, an annotated tumor region can be obtained one of concurrently with method or operations 100, 200, 300, 600, 2000, or 2200 (for example, via a system, apparatus, computer, or medical imaging device implementing method or operations 100, 200, 300, 600, 2000, or 2200) or prior to method or operations 100, 200, 300, 600, 2000, or 2200, or other operations described herein.

Figure 3:
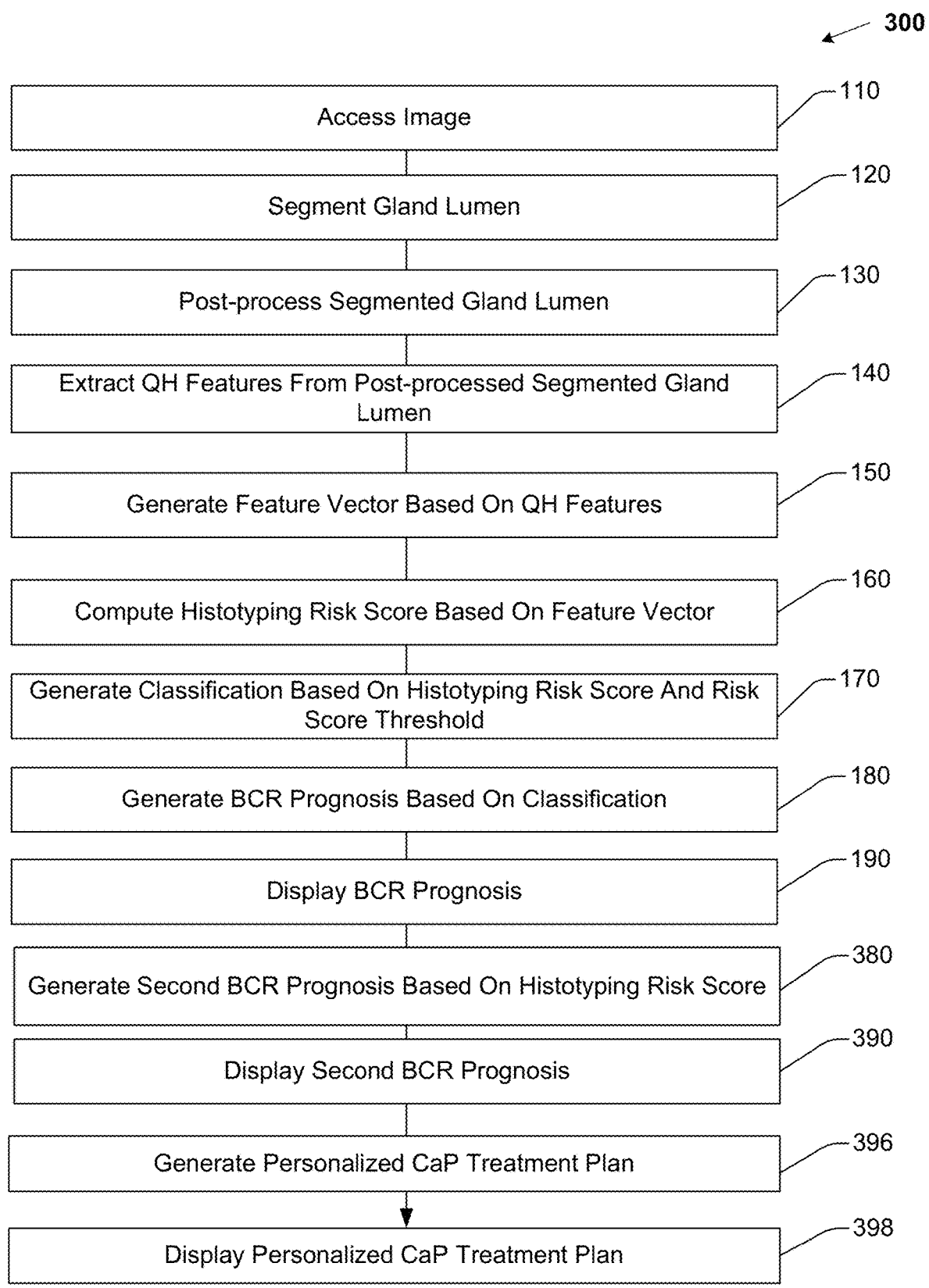
FIG. 3 illustrates a workflow diagram of an example method or set of operations according to various embodiments discussed herein.

FIG. 3 illustrates a set of operations 300 that is similar to operations 100 or 200, but that includes additional elements and details. The set of operations 300 includes operations 110-190. Operations 300 further includes, at 380, generating a second BCR prognosis based, at least in part, on the histotyping risk score. Operations 300 may further include, at 390, displaying the second BCR prognosis. The second BCR prognosis may be, in various embodiments, a continuous histotyping prognosis. For example, in one embodiment, where the histotyping risk score associated with a first patient has a value within the range [−0.72, 0.46], the second BCR prognosis may comprise a prognosis of increased risk of BCR where the histotyping risk score has a higher value, for example, 0.4. In this example, for a patient associated with a histotyping risk score having a lower value, for example, −0.5, the second prognosis may comprise a different prognosis of a lower risk of BCR. Other ranges may be employed.

The set of operations 300 may further include, at 396, generating a personalized CaP treatment plan. The personalized CaP treatment plan may be generated for the patient of whom the digitized H&E image was acquired based, at least in part, on the classification, the first BCR prognosis, or the second BCR prognosis, and optionally on one or more of the histotyping risk score, or the digitized H&E image. Defining or generating a personalized CaP treatment plan facilitates delivering a particular treatment that will be therapeutically active to the patient, while minimizing negative or adverse effects experienced by the patient. For example, the personalized CaP treatment plan may suggest a surgical treatment, may define a pharmaceutical agent dosage or schedule and/or other recommendations for CaP management, for a patient, wherein the specific recommendation can depend on a classification (e.g., high-risk of BCR) or prognosis associated with the patient. Generating the personalized CaP treatment plan includes acquiring electronic data, reading from a computer file, receiving a computer file, reading from a computer memory, or other computerized activity not practically performed in the human mind.

The set of operations 300 can further include, at 398, optionally displaying the personalized CaP treatment plan according to embodiments described herein.

Figure 5:
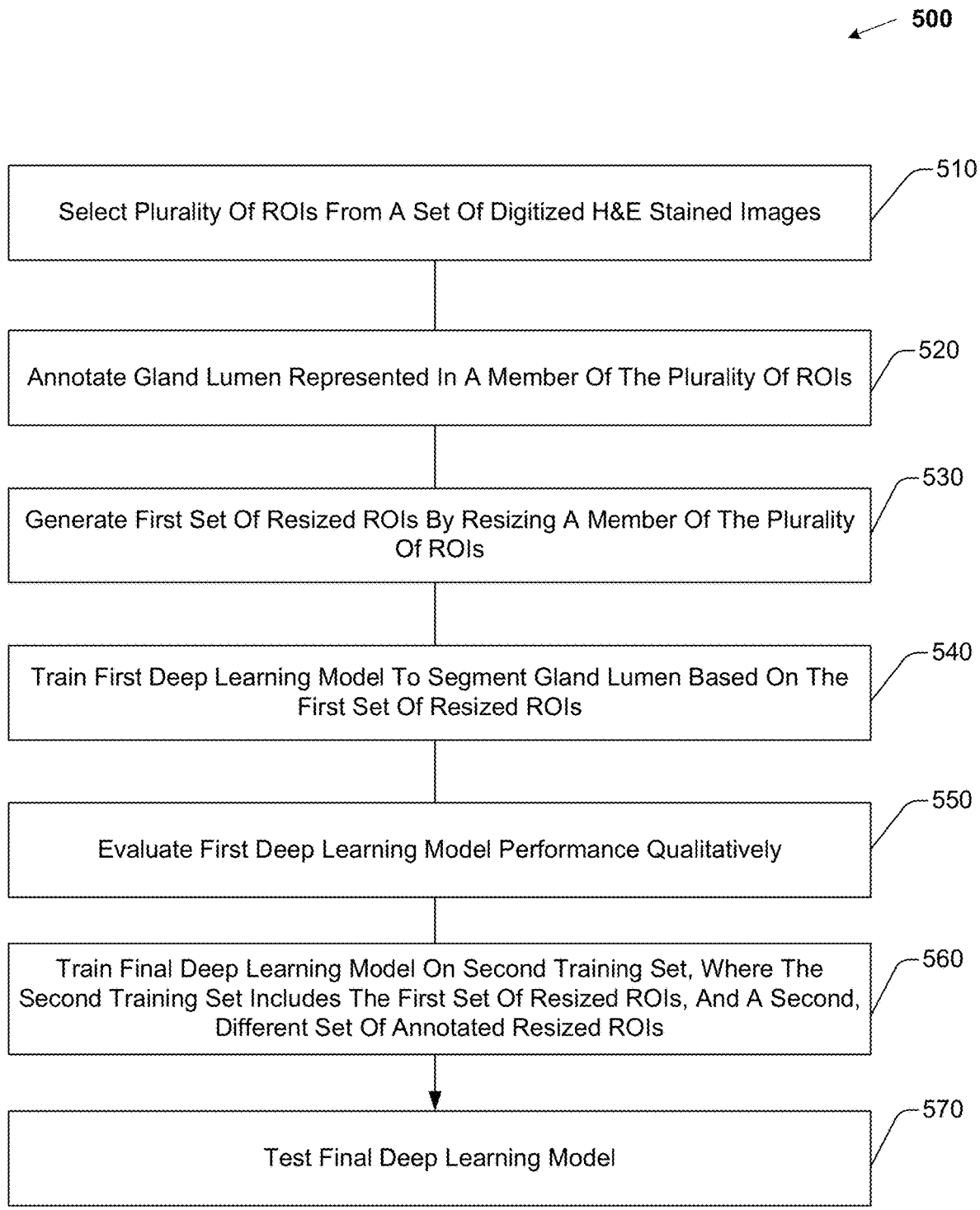
FIG. 5 illustrates a workflow diagram of an example method or set of operations according to various embodiments discussed herein.

Embodiments may train a deep learning model to segment gland lumen represented in digitized H&E stained imagery of tissue demonstrating CaP. FIG. 5 illustrates one example set of operations 500 for training a deep learning model to segment gland lumen represented in digitized H&E stained imagery of tissue demonstrating CaP. Operations 500 include, at 510, selecting a plurality of regions of interest (ROIs) from a set of digitized H&E stained images of tissue demonstrating CaP. In one embodiment, twenty nine (29) 2000×2000 pixel ROIs at 0.5 microns-per-pixel (20× magnification) are selected from the tumor regions of twenty nine (29) slides of a training set of digitized H&E stained images. ROIs may be chosen to represent a range of tissue morphology, for example cancers of various cancer grades, tissue preparation artifacts, areas of varying glandular density, areas of glandular atrophy, and areas of varying lymphocytic infiltration. Members of the set of digitized H&E stained images may be acquired across different institutions, or may have been acquired using different acquisition parameters.

Operations 500 also includes, at 520, annotating a gland lumen represented in a member of the plurality of ROIs. In one embodiment, gland lumen may be annotated using machine learning or deep learning techniques. A gland lumen includes a lumen boundary. In another embodiment, annotations may be performed by an expert human pathologist. In one embodiment, annotations may be performed using QuPath v0.12. In one embodiment, annotations may be cleaned to increase fidelity to the lumen boundary. In another embodiment, a set of digitized H&E stained images may be accessed that has gland lumen annotated prior to the execution of operations 500. For example, a set of digitized H&E stained images may be accessed that has gland lumen already annotated can be obtained via a computer, apparatus, system, or medical imaging device one of concurrently with method or operations 500 (for example, via a medical imaging device implementing method or operations 500) or prior to method or operations 500, or other operations described herein.

Operations 500 also includes, at 530, generating a first set of resized ROIs by resizing a member of the plurality of ROIs. In one embodiment, generating the set of resized ROIs comprises resizing a member of the plurality of ROIs to one µm per pixel. In another embodiment, an ROI may be resized to other sizes, including, for example, 2 microns-per-pixel. By reducing the number of pixels in the image, embodiments facilitate faster training of the deep learning model and reduce the time needed to apply the model to a new image, thereby improving the performance of the apparatus, system, or computer implementing embodiments described herein. In one embodiment, generating the first set of resized ROIs includes resizing all the members of the plurality of ROIs. In another embodiment, generating the first set of resized ROIs includes resizing a threshold number of the members of the plurality of ROIs, for example, 75% or 90% of the members of the plurality of ROIs. Operations 500 also includes, at 540, training a first deep learning model to segment a gland lumen based on the first set of resized ROIs. In one embodiment, the first deep learning model is trained using the first set of resized ROIs. In this embodiment, the first deep learning model is a modified UNet deep-learning model, and twenty nine (29) ROIs as selected at step 510 are employed.

Operations 500 also includes, at 550, evaluating the first deep learning model performance. In one embodiment, evaluating the first deep learning model performance includes selecting and annotating a set of additional ROIs which display morphology similar to that on which the deep learning model performed poorly. In one embodiment, identification of morphologically similar images comprises qualitatively identifying attributes of the ROI, such as tumor grade, glandular appearance, and cell-type frequency, and locating visually similar ROIs not yet included in the model training set. In one example, poor performance is defined as a substantially lower per-pixel accuracy than other images in the set of ROIs, or poor performance may be determined by a qualitative examination revealing large areas of incorrect segmentation. In one embodiment, the deep learning model is evaluated using a set of an additional twelve (12) 2000 pixel×2000 pixel ROIs which displayed morphology similar to that on which the first deep learning model performed poorly.

Operations 500 also includes, at 560, training a final deep learning model on a second training set, where the second training set includes the first set of resized ROIs, and a second, different set of annotated resized ROIs, where the second, different set of annotated resized ROIs is selected based on the evaluated first deep learning model performance. In one embodiment, generating the second different set of annotated resized ROIs includes resizing a member of the plurality of ROIs to one μm per pixel. In one embodiment, the final deep learning model is trained on a set of 41 annotated ROIs, while in another embodiment, another, different number of annotated ROIs may be employed.

Figure 11:
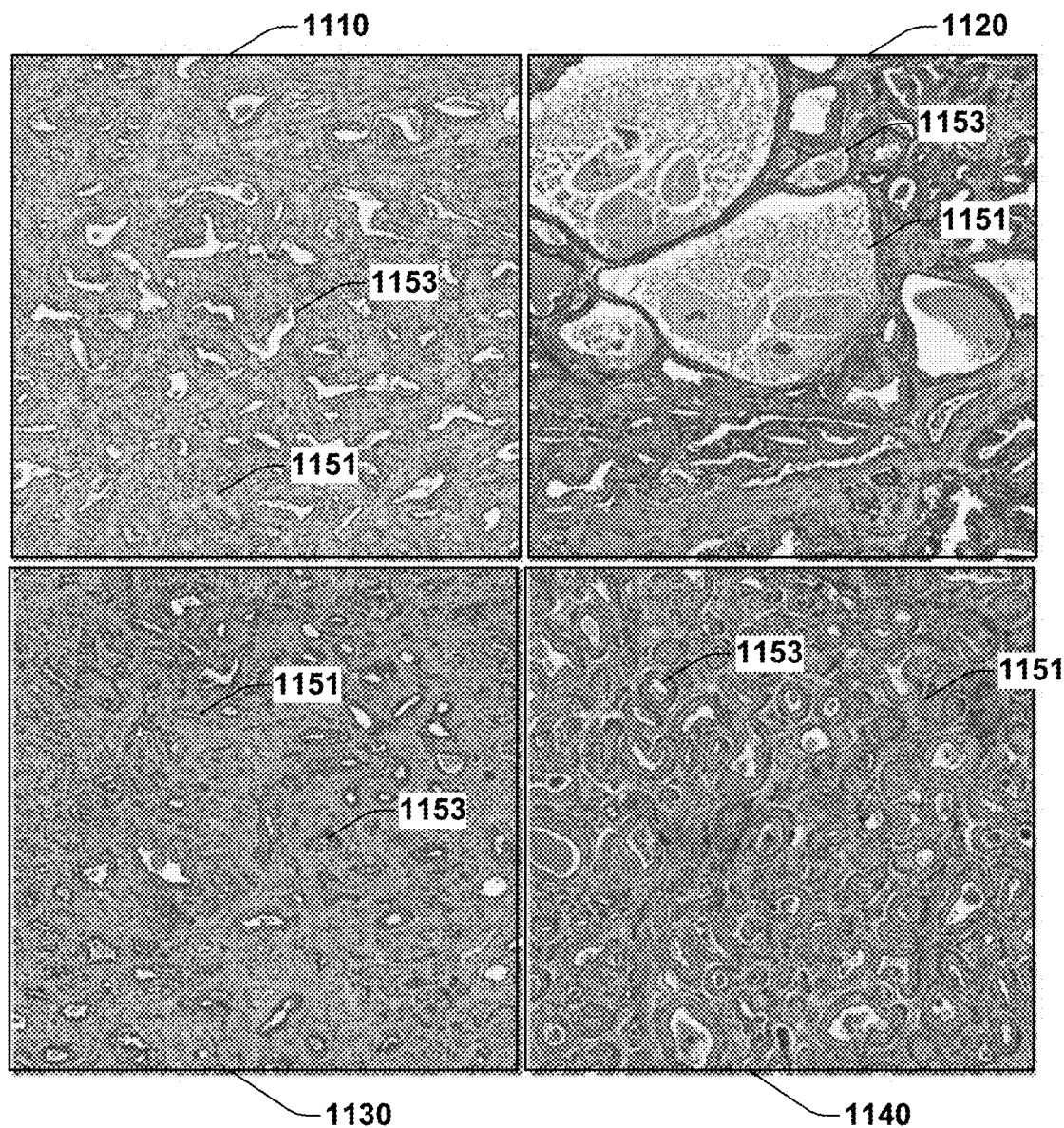
FIG. 11 illustrates ground truth annotations and segmentation results on held-out test images.

Operations 500 further includes, at 570, testing the final deep learning model. Testing the final deep learning model may include testing the final deep learning model on a set of held-out testing images. In one embodiment, four ROIs, for example ROIs 1110, 1120, 1130, and 1140, illustrated in FIG. 11, are used for testing the deep learning model. In one embodiment, FIG. 11 illustrates ground truth annotations 1151 (green) and segmentation results 1153 (blue) for four held-out test images 1110, 1120, 1130, and 1140. In this embodiment, the final deep learning model achieved a pixel-wise true positive rate of 0.97 and a true negative rate of 0.97 on these four held-out test images 1110, 1120, 1130, and 1140. In one embodiment, the final deep learning model is the model in the epoch having the minimum loss function value on the four held out images 1110, 1120, 1130, and 1140. In this embodiment, the final deep learning model had a depth of four (4) with a total of 1,928,450 parameters. In one embodiment, the optimal deep learning model was reached after 290 epochs, which was reached after 103.5 minutes using an Nvidia Titan Xp GPU.

Figure 6:
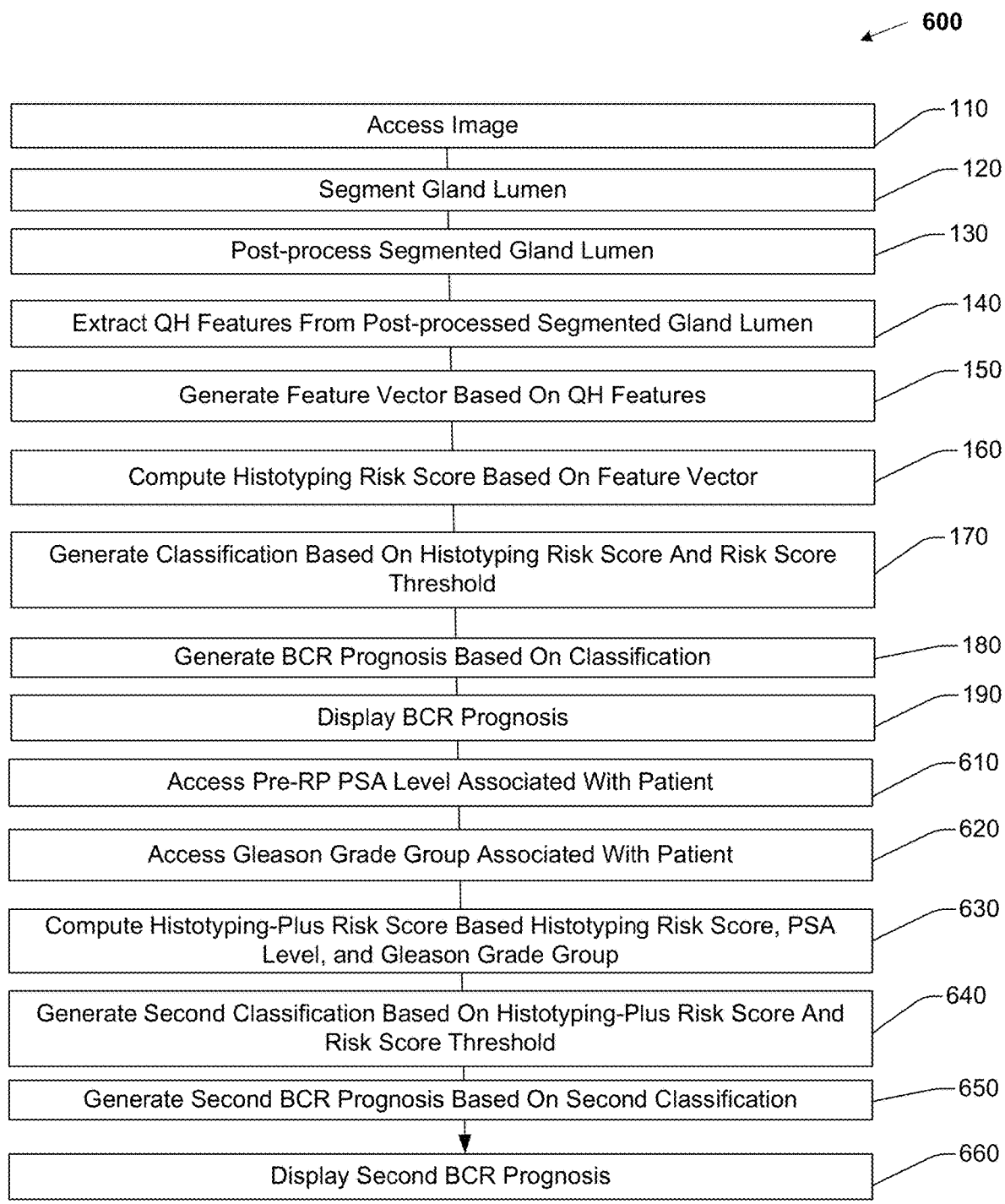
FIG. 6 illustrates a workflow diagram of an example method or set of operations according to various embodiments discussed herein.

Embodiments may compute a CaP BCR prognosis based on the histotyping risk score and further based on clinical factors associated with the patient. Embodiments may compute a CaP BCR prognosis based on a histotyping-plus risk score, where the histotyping-plus risk score is computed based on the histotyping risk score and additionally on clinical factors associated with the patient. Clinical factors associated with the patient may include, for example, a pre-radical prostatectomy (RP) serum prostate specific antigen (PSA) level, or a Gleason grade group. In another embodiment, a clinical factor(s) associated with the patient may include another, different clinical factor(s), including, for example, surgical margin positivity, number of positive lymph nodes, patient age, or seminal vesicle invasion status. FIG. 6 illustrates an example set of operations 600. Operations 600 are similar to operations 100 but include additional steps. Operations 600 includes operations 110-190, and further includes, at 610 accessing a pre-RP serum PSA level value associated with the patient. For example, the patient may have, prior to implementation of operations 600, undergone pre-operative, for example, pre-radical prostatectomy, serum prostate specific antigen testing. In one embodiment, the PSA level value may be defined in ng/mL.

Operations 600 also includes, at 620, accessing a Gleason grade group value associated with the patient. For example, in one embodiment, a Gleason grade group value may be computed one of concurrently with method or operations 600 (for example, via a medical imaging device implementing method or operations 600) or prior to method or operations 600, or other operations described herein, based on the digitized image. In one embodiment, the Gleason grade group value may have a value of 1, 2, 3, 4, or 5.

Operations 600 also includes, at 630, computing a histotyping-plus risk score. The histotyping-plus risk score may be computed as a function of the histotyping risk score, the PSA level value, and the Gleason grade group value. In one embodiment, computing the histotyping-plus risk score includes generating a second feature vector, where the second feature vector includes the value of the histotyping risk score, the pre-operative serum PSA level in ng/mL, and four binary variables corresponding to whether the patient was assigned Gleason grade group 2, 3, 4, or 5, respectively. The second feature vector is multiplied by the β values from the trained Histotyping-plus model according to techniques described herein. In one embodiment, the nonzero elements of the β vector correspond to Histotyping score, pre-operative PSA level, Gleason grade group 3, and Gleason grade group 4. The sum of the products of the feature vector and β values is the Histotyping-plus risk score. In another embodiment, the nonzero elements of the β vector may correspond to other, different Gleason grade groups, or other different clinical factors, including, for example, surgical margin positivity, number of positive lymph nodes, patient age, or seminal vesicle invasion status.

Operations 600 also includes, at 640, generating a second classification of the patient as BCR high-risk or BCR low-risk based on the histotyping-plus risk score, and a histotyping-plus risk score threshold. In one embodiment, the histotyping-plus risk score threshold has a value of 1.331. In another embodiment, the histotyping-plus risk score threshold may have another, different value, including, for example, 1.1 or 1.5, or other value.

In one embodiment, generating the second classification includes applying a histotyping-plus risk score threshold identified on the training set to the histotyping-plus risk score computed at 630 to stratify or categorize the patient as BCR low-risk or BCR high-risk according to whether the histotyping-plus risk score is less than (<) the histotyping-plus risk score threshold value, or greater than or equal to (>=) the histotyping-plus risk score threshold value. In one embodiment, the histotyping-plus risk score threshold has a value of 1.331. In another embodiment, the histotyping-plus risk score threshold may have another, different value. The histotyping-plus risk score threshold may be determined based, at least in part, on a range selected from within the range the histotyping-plus risk score is obtained, for example, [−1.210, 2.510], [−1.5, 3], [−0.5, 0.5], [−1, 1], or other range. The histotyping-plus risk score threshold may be computed according to various techniques described herein. For example, the histotyping-plus risk score threshold may, in one embodiment, be determined as the threshold that maximizes the hazard ratio in BCR-free survival time between histotyping-plus low-risk and histotyping-plus high-risk patients.

Operations 600 also includes, at 650, generating a histotyping-plus BCR prognosis based, at least in part, on the second classification. For example, generating the histotyping-plus BCR prognosis may include, for example, generating a prognosis that the patient is likely to experience BCR, where the patient is classified as BCR high-risk, or generating a prognosis that the patient is unlikely to experience BCR, where the patient is classified as BCR low-risk. In one embodiment, the histotyping-plus BCR prognosis is prognostic of BCR in CaP with: p<0.001, HR=3.23, 95%, CI: 1.68-6.21, and concordance index=0.75.

Operations 600 further includes, at 660, displaying the histotyping-plus BCR prognosis according to various techniques described herein.

Techniques and aspects of various embodiments are further explained below, in connection with an example embodiment that facilitates, for a patient demonstrating CaP, generating a BCR prognosis associated with the patient, or classifying the patient as a BCR high-risk patient or a BCR low-risk patient based on pathology imagery, including digitized H&E imagery, associated with the patient.

Example Use Case: Computerized Histomorphometric Features of Tumor Morphology from Routine Hematoxylin and Eosin Slides are Prognostic in Prostate Cancer An example embodiment included training a machine learning model to distinguish CaP patients with a low-risk of BCR from CaP patients with a high-risk of BCR, based on example H&E stained imagery of tissue demonstrating CaP, and quantitative morphology features extracted from the digitized H&E stained imagery. In this example, a study population consisted of n=896 patients from six sources: the University of Pennsylvania (UPenn), University Hospitals Cleveland Medical Center (UH), New York Presbyterian Hospital/Weill Cornell Medical Center (WCM), the University of Turku (UTurku), the Cancer Genome Atlas (TCGA), and Icahn School of Medicine at Mount Sinai (MS). Patient images were digitized on a variety of whole slide scanners, described in table 700 illustrated in FIG. 7. TCGA patients previously identified as having discrepancies in outcome information were excluded.

In this example, patients were divided into a training set and a validation set. The training set was composed of n=70 UPenn patients and n=145 UH patients. Within the UPenn cohort were two sub-cohorts, with 35 patients each. Each sub-cohort was collected a different time. The validation set consisted of the remaining n=681 patients from five sites (UPenn, WCM, UTurku, TCGA, MS). The UPenn patients were split between training and validation sets based on the scanner used to digitized the slides. The training set was selected to include approximately a quarter of the overall study dataset while containing patients from multiple institutions to enable analysis of feature stability across staining and scanning differences.

Figure 9:
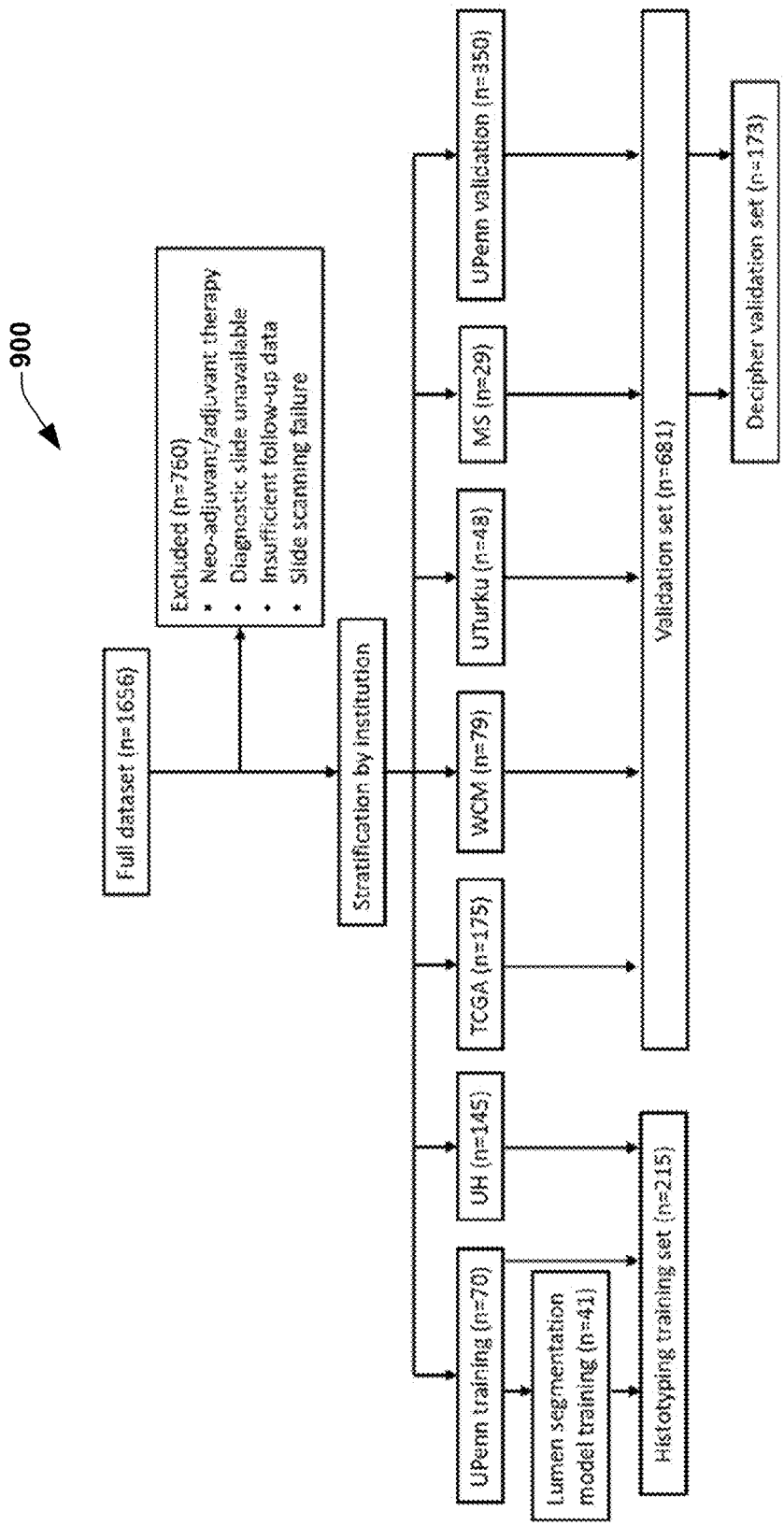
FIG. 9 illustrates a CONSORT diagram of clinical data associated with exemplary training cohorts.

In this example, the study cohorts are summarized in table 800 of FIG. 8, and FIG. 9. Table 800 illustrated in FIG. 8 illustrates clinical data for the 896 patients included in the study in this example. FIG. 9 illustrates a CONSORT diagram 900 of study cohorts in this example. Patients were included in this study if they had both a successfully digitized diagnostic slide and post-RP PSA test results available for no fewer than 30 days post-surgery. Patients who received neo-adjuvant or adjuvant therapy were excluded from the study. Patients were considered to have experienced BCR after two consecutive PSA serum tests >0.2 ng/mL. Non-BCR patients were censored at the date of last available PSA test.

In this example, a subset of the validation set consisting of 144 UPenn and 29 MS patients had Decipher genomic classifier results available and were used to compare embodiments employing Histotyping as described herein to Decipher. This cohort of UPenn patients consisted of all patients consenting to research who were operated on by the same single surgeon, respectively, before Jul. 1, 2017 who had PSA follow-up information and Decipher score results available.

In this example, the highest grade slide, for UTurku patients, or diagnostic slide, for all other sources, of each patient was digitized in a whole-slide scanner. In this example, for all cases, the slide and tumor nodule used were determined by a genitourinary pathologist. A single representative cancerous region, selected to include the highest grade cancer on the slide, was annotated on each digital image. Training set images also had a representative non-cancerous region annotated for the feature stability filtering step of model training. In embodiments described herein, automated techniques, including deep learning techniques, may be employed to annotate a cancerous or tumoral region, or a representative non-cancerous region.

Figure 10:
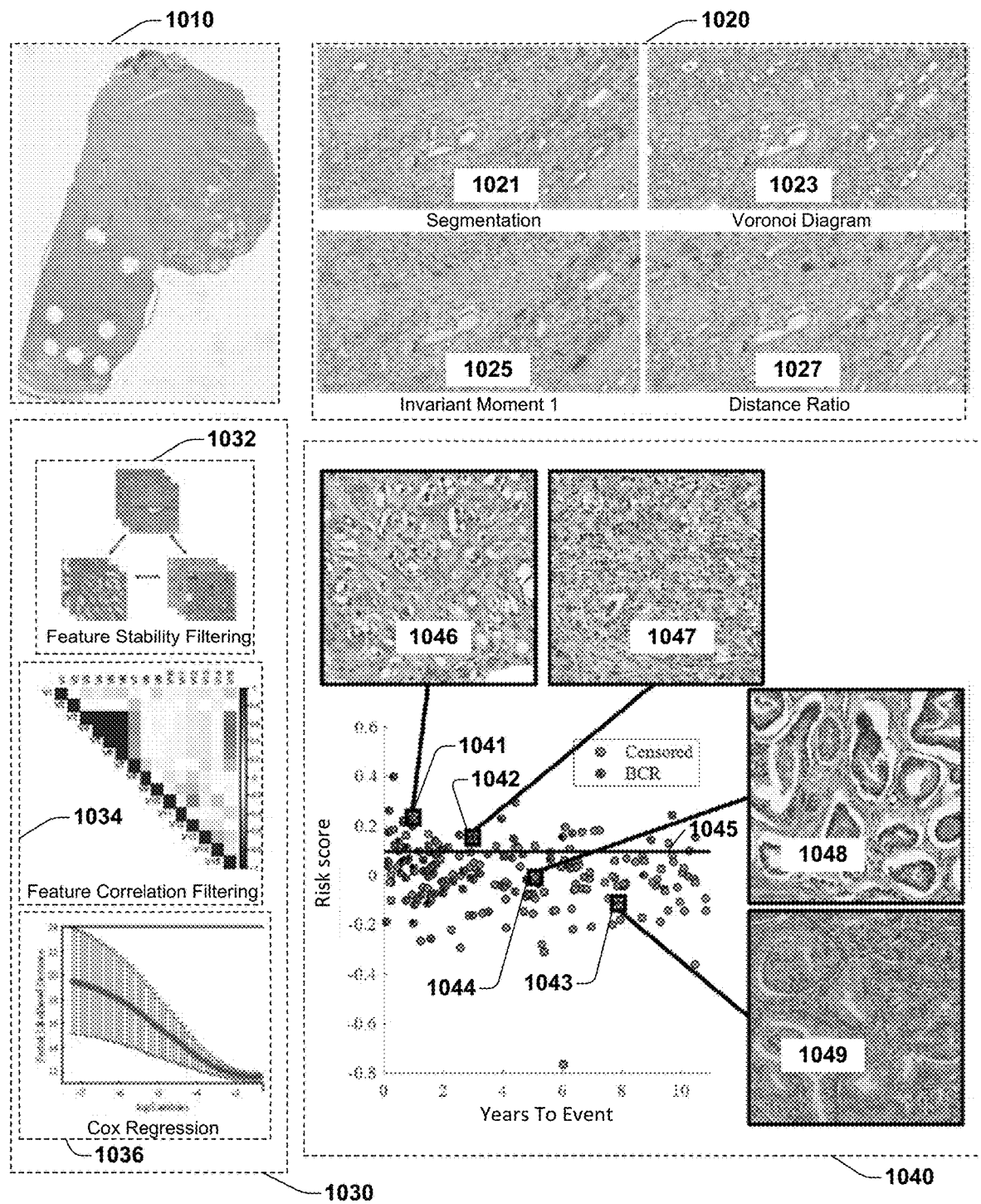
FIG. 10 illustrates an exemplary workflow for histotyping according to various embodiments discussed herein.

FIG. 10 illustrates an example workflow according to embodiments described herein. FIG. 10 illustrates, at 1010, annotation of a representative tumor region on a whole-slide image. FIG. 10 also illustrates, at 1020, results of automated gland segmentation 1021 and feature visualizations from a region of interest in the annotated lesion. Illustrated at 1023 is a Voronoi diagram, constructed by edges which are equidistant from adjacent glands. Illustrated at 1025 is the first invariant moment, which is equivalent to moment of inertia. Further illustrated is the distance ratio at 1027, which is the ratio of a gland's average radius to its maximum radius. For clarity of illustration, in the first invariant moment illustrated at 1025 and distance ratio illustrated at 1027, glands are shaded according to their feature values.

FIG. 10 also illustrates, at 1030, steps of model training of a classifier for generating a prognosis of BCR in CaP, where features extracted from segmented gland lumen are filtered for stability at 1032 using the three cohorts of the training set. A Cox regression model is then fitted using 10-fold elastic-net regularization, illustrated at 1036. In one example, model training may additionally include correlation filtering, illustrated at 1034.

FIG. 10 further illustrates, at 1040, results of model training. In this example, each patient of the n=263 training set is represented as a dot in the scatter plot, with patients who had BCR as red dots, for example dots 1041 and 1042, and censored patients as blue dots, for example dots 1043 and 1044. Dots are located on the x-axis (horizontal axis) at their time of BCR or time of last PSA test and on the y-axis (vertical axis) at their Histotyping risk score from the Cox regression model. The stratification threshold or histotyping risk score threshold identified on the training set is shown as a horizontal black line 1045 and is used to classify patients as BCR low-risk or BCR high-risk. Regions of interest from patients at various risk scores are shown in boxes 1046, 1047, 1048 and 1049.

In this example, gland lumen segmentation was performed by a deep learning model. In one example, a modified UNet architecture may be employed, while in another example, other deep learning model architectures may be employed. In this example, segmentation of gland lumen represented in the imagery was performed by a modified UNet-inspired deep learning model according to various techniques described herein. In this example, the deep learning segmentation model was trained on 41 1000×1000 pixel regions cropped from 37 training slides annotated for gland lumen. On the four regions held out for testing, illustrated in FIG. 11 at 1110, 1120, 1130, and 1140, the model yielded a per-pixel true positive rate and true negative rate of 0.97. Images were resized to 1 MPP (equivalent to 10× magnification) for lumen segmentation. In this example, the model was then applied to all 896 images, and the segmentation results were visually verified to be suitable for feature extraction. In another example, the regions cropped from the training slides may have other, different dimensions, for example, 2000×2000 pixels. Other magnification levels, including, for example, 20× (0.5 microns per pixel) or 5× (2 microns per pixel), may be employed by embodiments described herein.

In this example, a total of 242 features were extracted from the largest tumor region on each patient slide, of which a subset of nine (9) features were used in Histotyping. 216 of these features were descriptors of gland morphology and architecture and were extracted from the gland segmentations. 26 Haralick texture features were extracted from the entire annotated tissue region, with no regard for the segmentations. In this example, these features were selected based on their past performance in prostate cancer grading and BCR prognosis. FIG. 12 illustrates a table 1200 of the subset of nine (9) QH features used in this example. In this example, the subset of nine (9) QH features includes a mean invariant moment 2 shape feature, a mean Fourier descriptor 4 shape feature, a standard deviation of smoothness shape feature, a median distance ratio shape feature, a $5^{th}$ percentile/$95^{th}$ percentile perimeter ratio feature, a $5^{th}$ percentile/$95^{th}$ percentile Fourier descriptor 1 feature, a $5^{th}$ percentile/$95^{th}$ percentile Fourier descriptor 6 feature, a skewness of edge length sub-graph feature, and a Haralick mean correlation feature.

Accounting for differences in slide preparation and artifacts caused by said differences is a problem in CaP BCR prognosis. For example, since patients, including patients in the study dataset, may originate from many institutions, there may be variability in specimen preservation, fixation, sectioning, and staining as well as slide digitization hardware based on the protocols and equipment at each institution. These sources of pre-analytic variation affect the final appearance of the slide images and could therefore affect the features extracted from these images.

Embodiments provide a solution or solutions to this problem of differences in slide preparation and artifacts caused by said differences. For example, in this example, features highly susceptible to site-specific factors were removed to improve model performance. This filtering was performed using the two sub-cohorts of the UPenn patients separately, as there were qualitative visual differences between the sub-cohorts, and all the UH patients. This analysis was restricted to the non-cancerous regions to eliminate the confounding effect of tumor morphology on stability calculations. These restrictions caused the three sub-cohorts used in this step to contain 36, 37, and 93 patients. In this example, three quarters of the patients in each sub-cohort were randomly selected and features were evaluated with the Wilcoxon rank sum test for a significant difference between each pairwise combination of cohorts. This random sub-sampling and comparison was repeated 1000 times. Features significantly different in more than 10% of these iterations were discarded.

In this example, features which passed stability filtering at 1032 were used to train a Cox regression model via 10-fold elastic-net regularization ($\alpha=0.5$) at 1036. Features were normalized using the training set to have a mean of 0 and standard deviation of 1 so that hazard ratios would be comparable across features. The $\beta$ values of the final model, containing 9 features, for example, the nine (9) QH features listed in table 1200, were then applied to the training and validation sets to obtain a risk score for each patient. In this example, nine (9) features were included in the model as that was the number of features which minimized the deviance in 10-fold cross validation during training. The output of this step was a histotyping risk score for each patient which could take on any value and was unbounded, though for all patients in this study in this example ranged from −0.76 to 0.42. Other ranges may be employed.

Embodiments may determine or employ a risk score threshold. In this example, to find the optimal risk score threshold for stratifying low-risk and high-risk patients, each midpoint of the risk scores of consecutive training set patients was considered. First, thresholds which yielded a group smaller than one-third of the training set or a logrank p-value >0.05 were discarded. Next, the set of thresholds which yielded the maximum absolute difference in median survival time between the groups was identified. From among identified thresholds, the identified threshold with the largest hazard ratio was selected and applied to the training and validation sets to create the Histotyping risk groups. In one embodiment, the risk score threshold value may be, for example, 0.0960. Other risk score threshold values may be employed, for example, 0.08, 0.1, or other value.

Embodiments may evaluate the performance of methods, operations, apparatus, or other embodiments for generating a CaP BCR prognosis. In this example, the performance of Histotyping was evaluated in the validation set using the separation in BCR-free survival time between the low-risk and high-risk groups by logrank p-value, by hazard ratio, and by concordance index (c-index). Model independence was evaluated in a Cox proportional hazards with Histotyping risk score, Gleason grade group, margin positivity, pathological tumor stage, and preoperative PSA. To further validate the added value of Histotyping, clinically low-risk and high-risk cohorts were analyzed separately to determine if Histotyping according to embodiments described herein added value on top of clinical stratifications. Histotyping results in two clinically stratified cohorts (Gleason grade group 3, margin negative) are discussed here.

In this example, the performance of embodiments described herein, (e.g., Histotyping) was compared to Decipher for BCR prognosis in the 173 patients of the validation set who had Decipher score information. Decipher scores were calculated based on the predefined 22-marker Decipher classifier. The Decipher score is a continuous score between 0 and 1, with the lowest scores indicating a lower risk of metastasis. Patients with high score (>0.6) were categorized as high risk, patients with 0.45-0.6 as average risk, and patients with <0.45 as low risk.

In this example, additionally, a second elastic-net penalized Cox regression model was constructed on the training set using Histotyping, preoperative PSA level, and Gleason grade group to create the Histotyping-plus model. These covariates were chosen for this experiment as they were available in n=148 training set patients, more than for any other pair of clinical covariates. The Histotyping-plus model was then validated on all n=173 patients of the Decipher validation set and compared to Decipher by c-index. For stratification into low-/high-risk groups, for example, BCR low-risk/BCR high-risk, a new decision threshold was chosen using the training set in the same process as for Histotyping. In one embodiment, the new histotyping-plus risk score threshold value is 1.331, while in another embodiment, other threshold values may be employed.

For example, in one embodiment, a pre-operative prostate specific antigen (PSA) value is obtained for a patient. In this example, a Gleason grade group associated with the patient is obtained. In this example, a continuous histotyping risk score is computed according to techniques described herein. In this example, then a Histotyping-plus feature vector is generated, where the Histotyping-plus feature vector includes the Histotyping risk score, the pre-operative serum PSA level in ng/mL, and four binary variables corresponding to whether the patient was assigned Gleason grade group 2, 3, 4, or 5, is multiplied by the $\beta$ values from a trained Histotyping-plus model. The nonzero elements of the $\beta$ vector correspond to Histotyping score, pre-operative PSA level, Gleason grade group 3, and Gleason grade group 4. Embodiments may compute the sum of the products of the feature vector and $\beta$ values to determine the Histotyping-plus risk score. In this example, the Histotyping-plus risk score threshold identified on the training set is applied to the computed Histotyping-plus risk score to classify the patient as BCR low-risk or BCR high-risk. A prognosis may then be generated based, at least in part, on the classification.

In this example, Histotyping was significantly prognostic of BCR in the training (p<0.001, HR=2.38, 95% CI: 1.37-4.15, c-index=0.63) and validation (p<0.001, HR=2.27, 95% CI: 1.59-3.26, c-index=0.66) sets. The nine (9) features selected by the Cox regression model on the training set are shown in Table 1200 in FIG. 12. Seven of nine (9) selected features were lumen shape features. The prevalence of shape features in the model is in part a product of the stability filtering. Although shape features accounted for 100 of the 242 (41%) features explored in this study, they were 37 of the 47 (79%) features which passed the stability filtering step.

Figure 13:
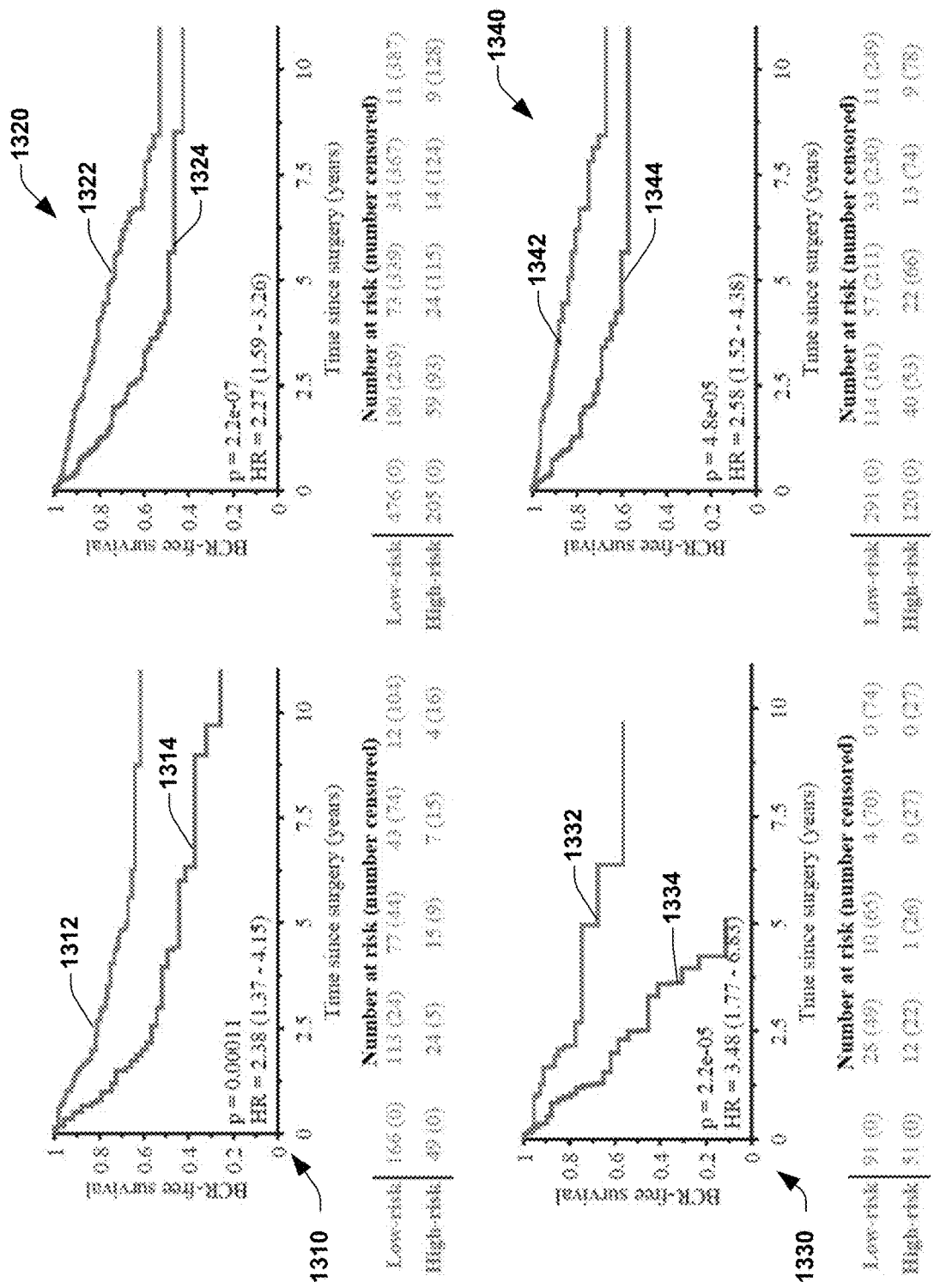
FIG. 13 illustrates Kaplan-Meier BCR-free survival plots of CaP patients according to various embodiments discussed herein.

In this example, embodiments employing Histotyping according to techniques described herein facilitate providing added value in at least patients with (a) Gleason grade group 3 (HR=3.48) and (b) negative surgical margins (HR=2.58). The BCR-free survival time of each risk category in the training set is shown in FIG. 13. In this example, Histotyping was significantly prognostic both as a continuous score (p<0.001, HR=1.33, 95% CI: 1.14-1.54) and as a categorical low/high-risk grouping (p<0.001, HR=2.38, 95% CI: 1.69-3.34) in a Cox proportional hazards model independent of Gleason grade group, margin status, pathological tumor stage, and preoperative PSA in the n=648 validation set patients with these clinical variables available, shown in Table 1400 in FIG. 14.

FIG. 13 illustrates Kaplan-Meier BCR-free survival plots 1310, 1320, 1330, and 1340 of patients categorized as Histotyping low-risk (1312, 1322, 1332, 1342) and Histotyping high-risk (1314, 1324, 1334, 1344) in the n=215 patient training set at 1310, the n=681 patient validation set at 1320, the n=142 patients of the validation set with Gleason grade group of 3 at 1330, and the n=411 patients of the validation set with negative surgical margins at 1340.

FIG. 14 includes table 1400, which illustrates Cox proportional hazard univariable (UVA) and multivariable (MVA) analysis of BCR including the Histotyping risk score with Gleason grade group, margin status, preoperative PSA, and pathological tumor stage in n=648 patients of the validation set.

Figure 15:
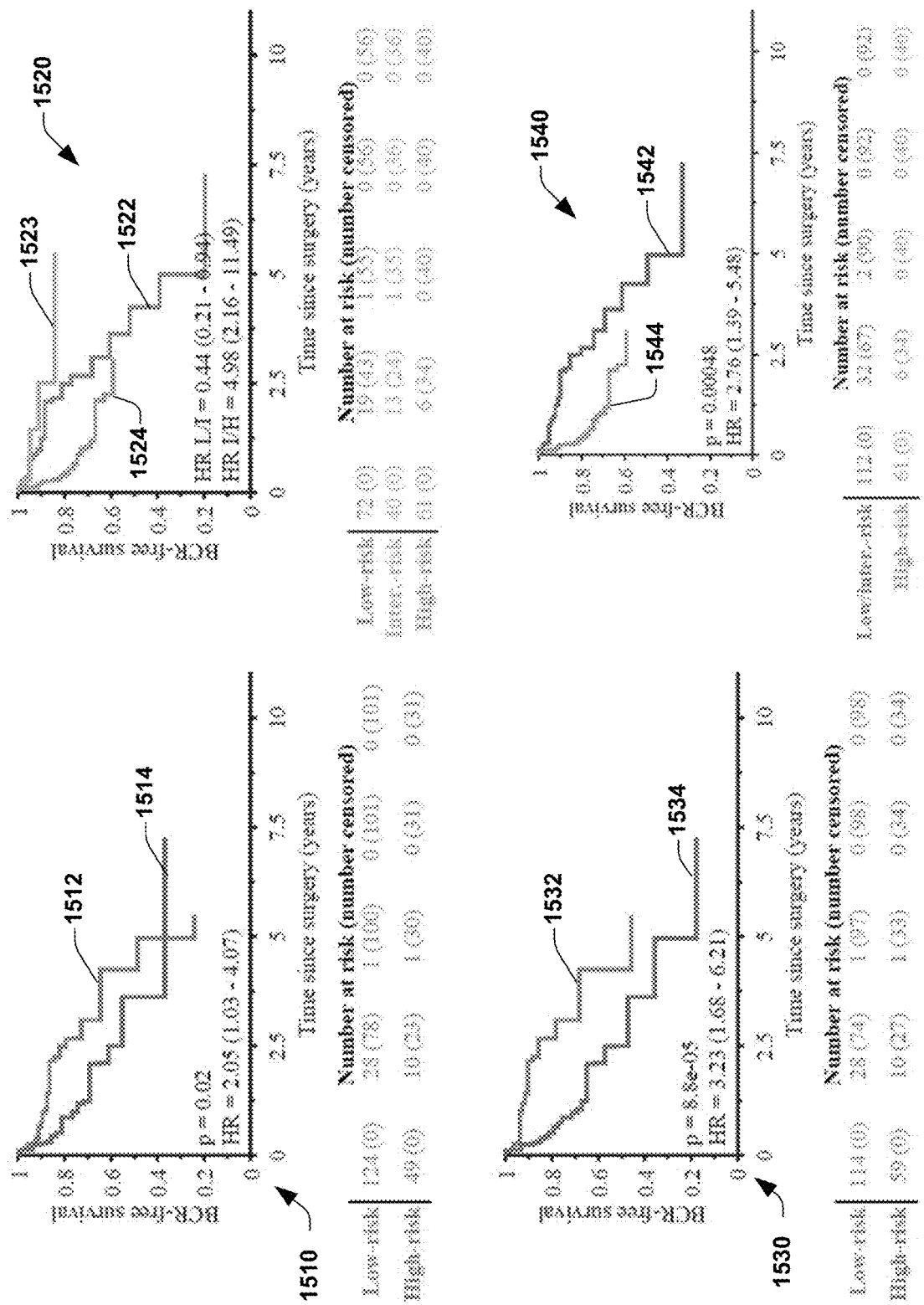
FIG. 15 illustrates Kaplan-Meier BCR-free survival plots of CaP patients according to various embodiments discussed herein.

FIG. 15 illustrates Kaplan-Meier BCR-free survival plots 1510, 1520, 1530, and 1540 of the 173 patients of the validation set who had Decipher score information. Patients are stratified by Histotyping at 1510, with low-risk plot 1512 and high risk plot 1514. Patients are stratified by Decipher risk groups at 1520, with low-risk plot 1522, intermediate-risk plot 1523, and high-risk plot 1524. Patients are stratified by Histotyping-plus, which incorporates Histotyping, pre-operative PSA, and Gleason grade group as described herein, at 1530, with low-risk plot 1532 and high risk plot 1534. Patients are stratified by Decipher risk groups at 1540, with low and intermediate risk as a single category plot 1542, and high-risk plot 1544.

In this example, for the n=173 patients who had Decipher score information, there was not a significant difference in BCR-free survival between Decipher low-risk and intermediate-risk patients (p=0.14). Based on this, for comparing Decipher to Histotyping categorically, Decipher low-risk and intermediate-risk patients were grouped together. Histotyping was prognostic in these patients (p=0.02, HR=2.05, 95% CI: 1.03-4.07, c-index=0.66) with performance comparable to Decipher (p<0.001, HR=2.76, 95% CI: 1.39-5.48, c-index=0.70).

In this example, embodiments generating a prognosis based on a Histotyping-plus risk score as described herein surpassed Histotyping alone and Decipher alone (p<0.001, HR=3.23, 95% CI: 1.68-6.21, c-index=0.75) using four covariates: Histotyping, preoperative PSA, pathological Gleason grade group 3 (relative to 1), and pathological Gleason grade group 4 (relative to 1).

In this example, embodiments employing Histotyping are prognostic of post-RP BCR-free survival, including in the validation cohort, independent of Gleason grade group, pre-operative prostate-specific antigen density, pathological tumor stage, and surgical margin positivity. Embodiments employing Histotyping according to techniques described herein, having a hazard ratio (HR) of 2.27 on the validation set is similar to that of current gold-standard BCR prognosis nomograms (HR=1.09-2.74). Furthermore, Histotyping-plus, incorporating Histotyping alongside Gleason grade group and preoperative PSA, had a higher concordance index than Histotyping alone and Decipher. Embodiments employing Histotyping according to techniques described herein added value in two clinically stratified cohorts which would be categorized as low-risk or intermediate-risk by existing methods: patients with Gleason grade group 3 and those with negative surgical margins. Embodiments employing Histotyping according to techniques described herein facilitate identifying patients who may benefit from adjuvant therapy but would not be likely to be recommended for additional therapy under current BCR prognosis schemes. Embodiments employing Histotyping according to techniques described herein facilitate identifying high-risk patients with low-risk clinical markers or intermediate-risk clinical markers due to the lower risk associated with additional adjuvant therapy versus de-intensifying therapy for clinically high risk patients.

Accurate post-surgery BCR prognosis, including, for example, post RP BCR prognosis, is a problem in treating CaP. Accurate post-surgery BCR prognosis has substantial implications for patient care and healthcare utilization. While the STAMPEDE trial has demonstrated that adjuvant therapy can improve patient survival after surgery, not every patient will benefit from further treatment. Current statistics suggest that ten high-risk CaP patients need to receive adjuvant therapy to avoid one death, indicating that current BCR prognosis tools are sub-optimal. The gold standard of these tools, nomograms, are driven by Gleason grading, which is limited by the power of human perception and has only moderate inter-reviewer agreement. Accordingly, there has been an increasing awareness of the need for an objective and accurate BCR prognosis tool. Companion diagnostic assays, such as the Decipher genomic test, have been validated for metastasis prognosis. These assays are tissue destructive, prohibiting retesting, and destroy irreplaceable human tissue. Though they may be prognostic, the long time required to obtain genetic testing results delays the start of adjuvant therapy. Additionally, molecular testing protocols are expensive and sophisticated, limiting their availability. For example, OncoType DX Prostate costs $4520, but still produces a net cost savings of over $2000 per patient by reducing the number of patients receiving treatment. Thus, embodiments described herein for generating a BCR prognosis may yield a large cost savings in addition to improved patient outcomes. Embodiments may further facilitate improved performance of BCR prognosis systems, apparatus, or processors, circuits, logics, or computers in which embodiments described herein may be implemented or practically integrated.

Embodiments described herein facilitate a QH-based assay, termed Histotyping, for CaP risk stratification or BCR prognosis generation. The Histotyping risk score according to embodiments described herein is significantly prognostic of BCR-free survival in the BCR validation cohort independent of Gleason grade group, pre-operative prostate-specific antigen density, pathological tumor stage, and surgical margin positivity. Histotyping according to embodiments described herein added value in two cohorts which would be categorized as low-risk by current methods: patients with Gleason grade group 2 and those with negative surgical margin. Histotyping according to embodiments described herein facilitates identification of patients who may benefit from adjuvant therapy but would not be likely to be recommended for additional therapy under current, existing BCR prognosis schemes. Identifying high-risk patients with low-risk clinical markers is a problem in CaP risk stratification. Embodiments facilitate providing improved outcomes in CaP due at least to improved identification of high-risk patients with low-risk clinical markers due, at least in part, to the lower morbidity risk associated with recommending additional adjuvant therapy relative to the risks of de-intensifying therapy for clinically high-risk patients. American Society for Radiation Oncology/American Urological Association (ASTRO/AUA) guidelines specifically recommend that adjuvant therapy be discussed with margin positive patients due to the lack of evidence that margin negative patients benefit from additional post-RP treatment. Histotyping according to embodiments described herein, has an HR of 2.27 on the validation set, and is thus comparable with studies of the performance of current gold-standard BCR prognosis nomograms on independent sets (HR=1.09-2.74). The concordance index of embodiments described herein (CI=0.66) is similar to the performance of the Kattan nomogram (CI=0.68). Embodiments thus provide a measurable improvement over existing methods, systems, apparatus, or other devices or approaches in reliably and accurately predicting patient outcome and improving treatment management in CaP.

Figure 16:
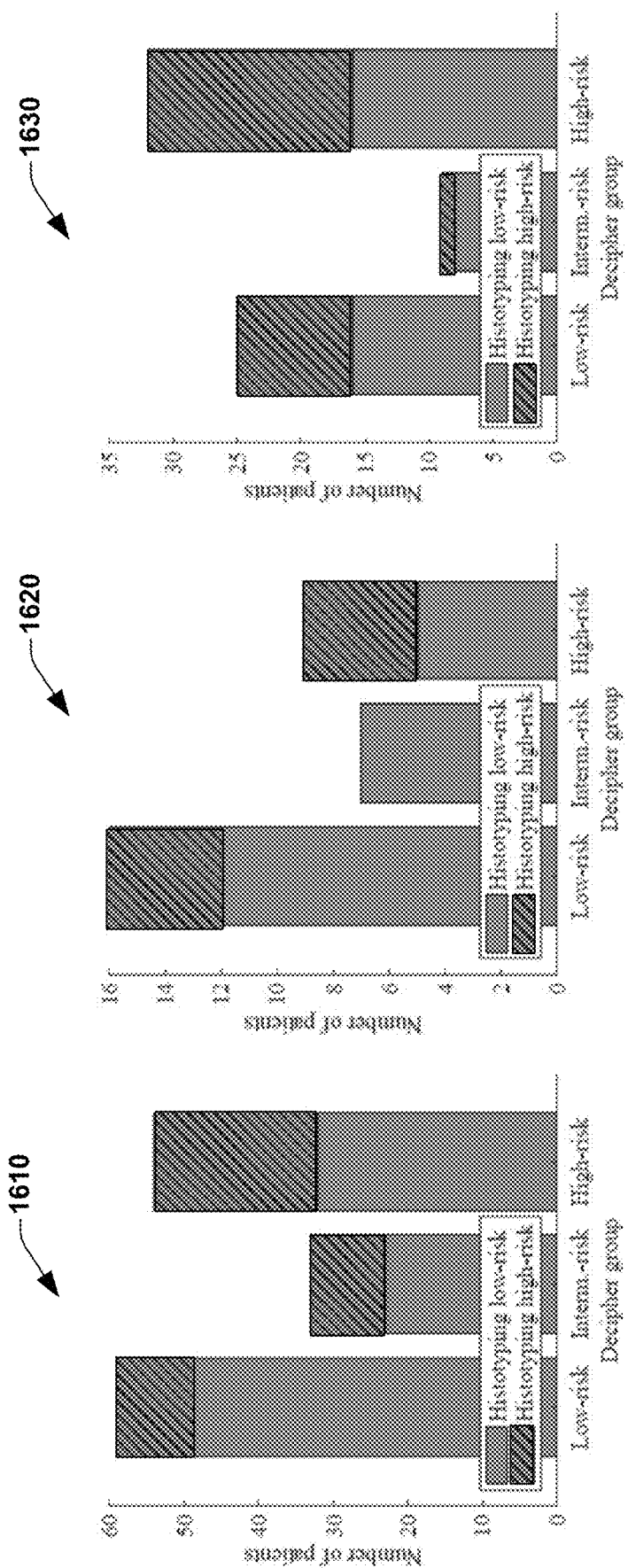
FIG. 16 illustrates concordance between Decipher and Histotyping risk categories in patients from different institutions.

In this example for the n=66 patients of the Decipher validation set, Histotyping according to embodiments described herein showed a strong concordance with Decipher. To investigate the concordance of Histotyping risk categories with Decipher risk categories, a set of N=66 patients from the Cleveland Clinic were analyzed alongside the patients of the validation set who had Decipher score information. BCR outcome information was not available for Cleveland Clinic patients, which is why those patients were not included in the validation set. The distribution of Histotyping risk scores for patients in each Decipher risk Category are shown in FIG. 16. Concordance between Decipher and Histotyping risk categories is illustrated in patients from University of Pennsylvania at 1610, Mount Sinai at 1620, and the Cleveland Clinic at 1630.

Embodiments provide for greater stability than existing approaches. Instability across imagery acquired from different institutions is a problem in CaP BCR prognosis generation. Some gland shape features are useful for cancer detection, grading, and BCR prognosis. However, while some existing approaches have found gland orientation and texture features to be useful in CaP risk assessment, those features did not appear in the top features of embodiments described herein. Histotyping according to embodiments described herein does not include these features partly due to their instability, with just a quarter of texture features and an eighth of orientation features passing the stability filtering step. Existing approaches which rely on unstable features may have worse results when using independent validation sets. Further distinguishing embodiments described herein from existing approaches, a BCR prognosis generated according to techniques described herein, for example, Histotyping, may be associated with Decipher test results, a validation not used in existing approaches.

In contrast to existing companion diagnostics approaches, embodiments described herein may require only a routinely acquired diagnostic H&E slide, a whole-slide scanner capable of scanning at a resolution of 1 MPP, and a moderately powerful desktop computer. Once the slide is created, Histotyping analysis can be completed in less than twelve (12) hours at a per-unit cost of nearly zero. Unlike other existing digital pathology approaches for risk assessment that use special stains or deep learning models with limited interpretability, the Histotyping assessment, including for example, classification of the patient as BCR low-risk or BCR high-risk, or generation of a BCR prognosis, according to embodiments described herein is directly driven by explainable descriptors, for example, the set of QH features, of tissue morphology from an H&E slide. Embodiments facilitate use of automated morphological analysis techniques as a companion diagnostic to augment existing methods and as a stand-in for areas where pathological expertise and expensive molecular tests are not available. Embodiments thus provide a solution to at least the problem of accurate post-surgery BCR prognosis, through the use of automated techniques for stratifying patients by BCR risk using a single H&E slide, and can identify a high-risk cohort among patients who would otherwise be classified as low-risk by existing approaches. Embodiments that generate a histotyping-plus-based BCR prognosis further based on routine PSA level tests or Gleason scoring facilitate a similarly improved solution to at least the problem of accurate post-surgery BCR prognosis.

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods or operations 100, 200, 300, 400, 500, 600, 2000, or 2200, or any other methods or operations described herein. While executable instructions associated with the listed methods or operations are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein related to distinguishing patients likely to experience BCR from patients unlikely to experience BCR in CaP, to generating a CaP BCR prognosis, generating a histotyping risk score, and other embodiments, are based on features that are not perceivable by the human eye, and their computation cannot be practically performed in the human mind. A machine learning classifier or deep learning model as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features, or compute prognoses that are based on the digitized images and extracted features and not on properties of tissue or the images that are perceivable by the human eye. Embodiments described herein can use a combined order of specific rules, elements, operations, circuits, logics, or components that render information into a specific format that can then be used and applied to create desired results more accurately, more consistently, and with greater reliability than existing approaches, thereby producing the technical effect of improving the performance of the machine, computer, or system with which embodiments are implemented or practically integrated.

Figure 17:
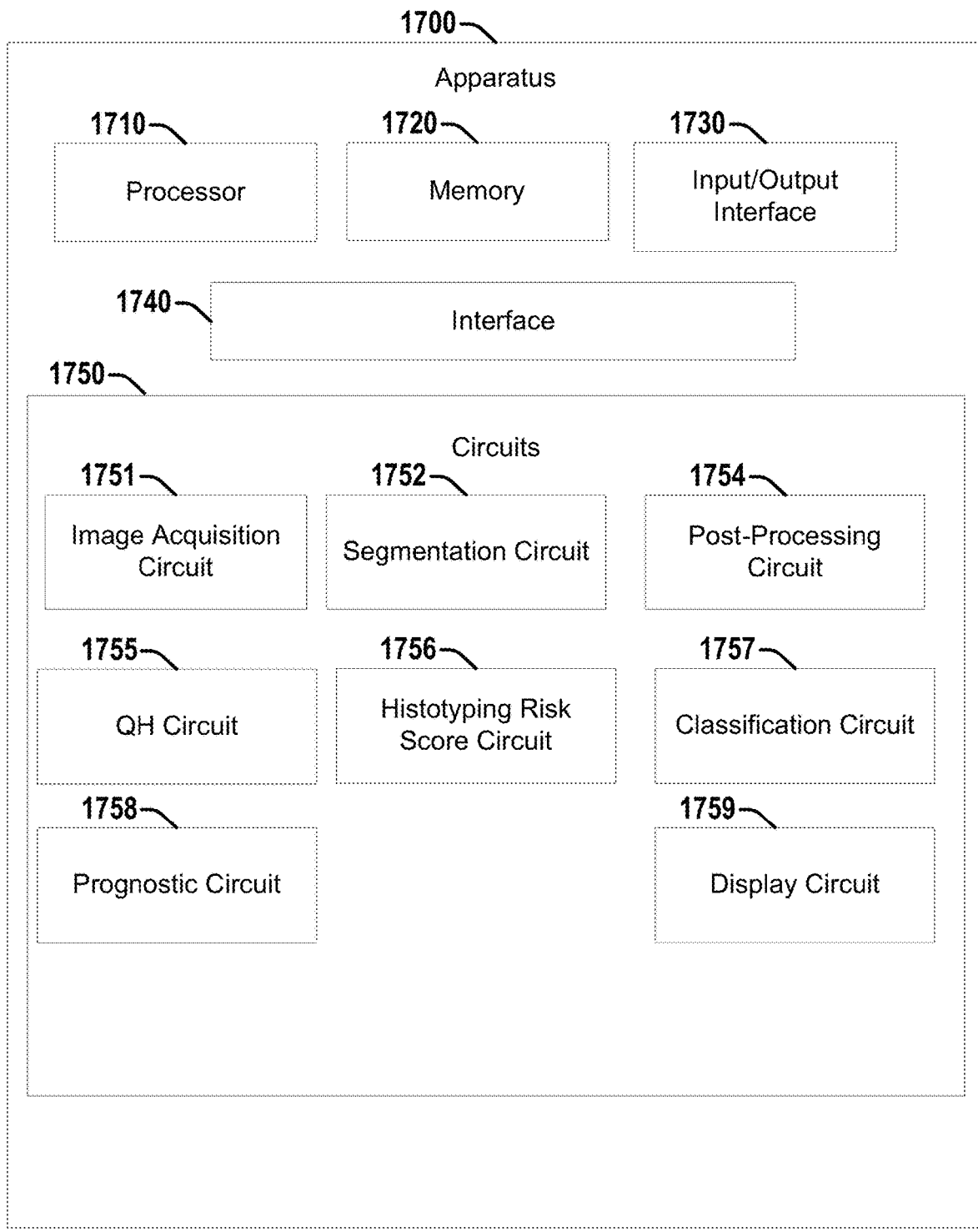
FIG. 17 illustrates a diagram of an example apparatus that can facilitate prognosis of BCR according to various embodiments discussed herein.

FIG. 17 illustrates an example apparatus 1700 that can facilitate generating a BCR prognosis associated with a patient, or classifying a patient as BCR low-risk or BCR high-risk in CaP, based on digitized pathology imagery, including for example, digitized H&E stained imagery, according to various embodiments discussed herein. Apparatus 1700 may be configured to perform various techniques, operations, or methods discussed herein. Apparatus 1700 may be configured to, for example, train a deep learning model, a machine learning classifier (e.g., quadratic discriminant analysis (QDA) classifier, linear discriminant analysis (LDA) classifier, logistic regression model classifier, a convolutional neural network (CNN) classifier, a support vector machine (SVM) classifier, etc.) based on training data to distinguish a patient as BCR low-risk or BCR high-risk in CaP, or employ such a trained machine learning classifier or deep learning model to generate a classification of a patient based on QH features extracted from digitized H&E stained imagery, or further based on clinical data associated with the patient. Apparatus 1700 may be configured to, for example, train a deep learning model to segment gland lumen represented in digitized H&E stained imagery. In one embodiment, apparatus 1700 includes a processor 1710, and a memory 1720. Processor 1710 may, in various embodiments, include circuitry such as, but not limited to, one or more single-core or multi-core processors. Processor 1710 may include any combination of general-purpose processors and dedicated processors (e.g., graphics processors, application processors, etc.). The processor(s) can be coupled with and/or can comprise memory (e.g., memory 1720) or storage and can be configured to execute instructions stored in memory 1720 or storage to enable various apparatus, applications, or operating systems to perform operations and/or methods discussed herein.

Memory 1720 is configured to store a digitized histopathology image associated with a patient, where the image includes a region of interest (ROI) demonstrating CaP. The digitized image may be, for example, a digitized H&E slide image. The digitized image has a plurality of pixels, a pixel having an intensity. In some embodiments, memory 1720 can store a training set or testing set of images. The training set or testing set of images may for example, comprise digitized H&E images showing CaP tissue, along with a known prognosis, or outcome (e.g., BCR, metastasis) for training a deep learning model or a classifier, for example, a machine learning model, QDA classifier, etc., to segment gland lumen represented in a digitized H&E stained image, or to generate a prognosis or determine a probability that the patient associated with the image is BCR high-risk or BCR low-risk, while in the same or other embodiments, memory 1720 can store a digitized H&E image of a patient for whom a prediction of BCR, a prognosis, a classification, or outcome is to be determined. Memory 1720 can be further configured to store one or more clinical features or other data associated with the patient associated with the digitized H&E image. For example, memory 1720 may be configured to store a Gleason grade group associated with the patient, a Gleason score, or a pre-operation PSA level associated with the patient.

Apparatus 1700 also includes an input/output (I/O) interface 1730; a set of circuits 1750; and an interface 1740 that connects the processor 1710, the memory 1720, the I/O interface 1730, and the set of circuits 1750. I/O interface 1730 may be configured to transfer data between memory 1720, processor 1710, circuits 1750, and external devices, for example, a medical imaging device such as an digital whose slide scanner, system, or apparatus.

The set of circuits 1750 includes an image acquisition circuit 1751, a segmentation circuit 1752, a post-processing circuit 1754, a quantitative histomorphometry (QH) circuit 1755, a histotyping risk score circuit 1756, a classification circuit 1757, a prognostic circuit 1758, and a display circuit 1759.

Image acquisition circuit 1751 is configured to acquire a digitized image of a region of tissue demonstrating CaP pathology. In one embodiment, image acquisition circuit 1751 is configured to acquire a digitized hematoxylin and eosin (H&E) stained image of a region of tissue demonstrating CaP pathology. The region of tissue includes a tumor region. The digitized image includes a plurality of pixels, a pixel having an intensity. The digitized image is associated with a patient. Acquiring or accessing the digitized H&E stained image may include accessing a digitized H&E stained image stored in memory 1720. In another embodiment accessing the digitized H&E stained image may include acquiring electronic data, reading from a computer file, receiving a computer file, reading from a computer memory, or other computerized activity not practically performed in the human mind.

Segmentation circuit 1752 is configured to generate a set of segmented gland lumen. In one embodiment, the segmentation circuit comprises a deep learning segmentation model trained to segment gland lumen represented in a digitized H&E stained image of a region of tissue demonstrating CaP. In one embodiment, the deep learning segmentation model is trained according to various techniques described herein. For example, the deep learning segmentation model may be trained according to operations 500. In one embodiment, the deep learning segmentation model is a modified UNet model. In one embodiment, segmentation circuit 1752 is configured to access a deep learning segmentation model stored in, for example, memory 1720.

Post-processing circuit 1754 is configured to generate a set of post-processed segmented gland lumen by post-processing the set of segmented gland lumen. Post-processing circuit 1754 may be configured to correct, re-label, or remove objects incorrectly labelled as segmented gland lumen from an initial post-processed set of segmented gland lumen according to techniques described herein. Post-processing circuit 1754 may be configured to remove artifacts from the set of segmented gland lumen. In one embodiment, post-processing circuit 1754 is configured to: define a set of post-processed segmented gland lumen, where the set of post-processed segmented gland lumen includes the members of the set of segmented gland lumen; determine if a member of the set of post-processed segmented gland lumen includes a non-lumen region. Post-processing circuit 1754 is further configured to, upon determining that the member of the set of post-processed segmented gland lumen includes a non-lumen region: re-label the non-lumen region as lumen. Post-processing circuit 1754 is further configured to determine an area of a member of the set of segmented gland lumen. Post-processing circuit 1754 is further configured to, upon determining that the member of the set of segmented gland lumen has an area less than a threshold area: remove the member of the set of segmented gland lumen from the set of post-processed segmented gland lumen; and determine a boundary of a member of the set of segmented gland lumen. Post-processing circuit 1754 is further configured to, upon determining that the boundary of the member of the set of segmented gland lumen is defined by a white pixel: remove the segmented gland lumen from the set of post-processed segmented gland lumen. In one embodiment, the threshold area is 4 $\mu m^2$. In another embodiment, the threshold area may have another, different value, for example, 3 $\mu m^2$, or 5 $\mu m^2$, or other value.

Quantitative histomorphometry (QH) circuit 1755 is configured to extract a set of QH features based, at least in part, on the set of post-processed segmented gland lumen. QH circuit 1755 is also configured to generate a feature vector based on the set of QH features. In one embodiment, QH circuit 1755 is further configured to normalize the feature vector according to various techniques described herein.

In one embodiment, the set of QH features includes at least nine features. In this embodiment, the set of QH features includes a set of gland lumen features, a set of sub-graph features, and a set of texture features. In this embodiment, the set of gland lumen features is based, at least in part, on the post-processed set of segmented gland lumen. In this embodiment, the set of texture features includes at least one texture feature extracted from the tumor region. In this embodiment, the set of sub-graph features includes at least one sub-graph feature extracted from the tumor region. In one embodiment, the set of QH features includes at least seven gland lumen shape features, at least one sub-graph feature, and at least one Haralick feature. In one embodiment, the set of QH features includes a mean invariant moment 2 feature, a mean Fourier descriptor 4 feature, a standard deviation of smoothness feature, a median distance ratio feature, a $5^{th}$ percentile/$95^{th}$ percentile perimeter ratio feature, a $5^{th}$ percentile/$95^{th}$ percentile Fourier descriptor 1 feature, a $5^{th}$ percentile/$95^{th}$ percentile Fourier descriptor 6 feature, a skewness of edge length sub-graph feature, and a Haralick mean correlation feature. In another embodiment, QH circuit 1755 may be configured to extract another, different number of QH features, or the set of QH features may include other, different QH features.

Histotyping risk score circuit 1756 is configured to compute a weighted sum of the feature vector. Histotyping risk score circuit 1756 is also configured to compute a histotyping risk score based on the weighted sum of the feature vector. In one embodiment, the histotyping risk score may be within a range of, for example, [−0.72, 0.46]. In another embodiment, the histotyping risk score may be within another, different range, for example, [−1, 1], or other range. In one embodiment, histotyping risk score circuit 1756 is configured to compute the histotyping risk score based on the weighted sum of the feature vector, where the feature vector is normalized according to techniques described herein. In one embodiment, histotyping risk score circuit 1756 is configured to compute the histotyping risk score by multiplying a normalized feature vector by a vector of β values. The vector of β values may be obtained from a histotyping model trained according to techniques described herein. In this embodiment, histotyping risk score circuit 1756 is further configured to compute the histotyping risk score by computing the sum of the products of the normalized feature vector and their corresponding β values.

Classification circuit 1757 is configured to generate a classification of the patient as biochemical recurrence (BCR) high-risk or BCR low-risk based on the histotyping risk score and a risk score threshold. In this embodiment, generating the classification based on the histotyping risk score and the risk score threshold includes generating a categorical classification. For example, classification circuit 1757 may be configured to categorize the patient as BCR low-risk if the histotyping risk score is less than (<) the risk score threshold value, or BCR high-risk if the histotyping risk score is than or equal to (>=) the risk score threshold value. In one embodiment, where the histotyping risk score may be within a range of, for example, [−0.72, 0.46], the risk score threshold value may be, for example, 0.0960. In this embodiment, a patient classified as BCR high-risk has a 1.95 times higher chance of BCR than a patient classified as BCR low-risk. In another embodiment, the risk score threshold value may be another, different value.

In various embodiments, the classification may include one or more of a most likely outcome (e.g., as determined based on the histotyping risk score, the risk score threshold, the set of QH features) such membership in a first class or second, different class, for example, BCR low-risk, BCR high-risk, or metastasis low-risk, metastasis high-risk, a probability or confidence associated with a most likely outcome; and/or associated probabilities/confidences associated with each of a plurality of outcomes.

Prognostic circuit 1758 is configured to generate a first BCR prognosis based, at least in part, on the classification. In one embodiment, prognostic circuit 1758 is further configured to generate a second BCR prognosis based on the histotyping risk score. In this embodiment, generating the second BCR prognosis based on the histotyping risk score includes generating a BCR prognosis based on a continuous classification. For example, when the histotyping risk score may be within a range of, for example, [−0.72, 0.46], an increase in the histotyping risk score of 0.1 is associated with a prognosis of 1.05 times higher risk of BCR. In another embodiment, the histotyping risk score may be within another, different range, for example [−1, 1], or other range.

Display circuit 1759 is configured to display at least one of the BCR prognosis, the classification, the histotyping risk score, the weighted sum of the feature vector, the feature vector, the set of QH features, the set of post-processed segmented gland lumen, or the digitized image. In one embodiment, display circuit 1759 is further configured to display the second BCR prognosis according to techniques described herein. Display circuit 1759 may be further configured to optionally display other data associated with the patient or associated with the operation of apparatus 1700.

Figure 18:
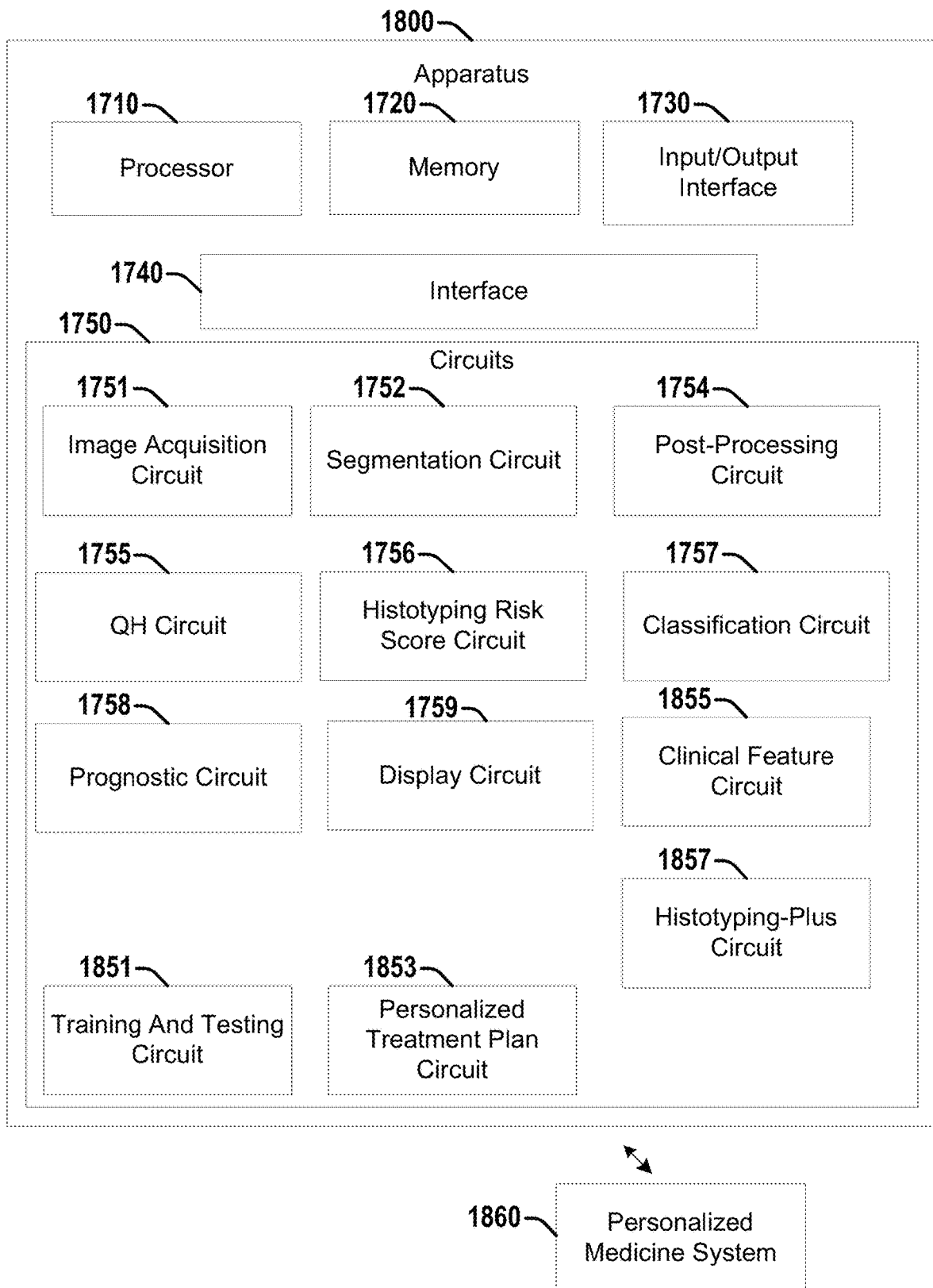
FIG. 18 illustrates a diagram of an example apparatus that can facilitate prognosis of BCR according to various embodiments discussed herein.

FIG. 18 illustrates an apparatus 1800 that is similar to apparatus 1700 but that includes additional elements and details. In one embodiment of apparatus 1800, the set of circuits 1750 further includes a CaP personalized treatment plan circuit 1853. CaP personalized treatment plan circuit 1853 is configured to generate a personalized CaP treatment plan based, at least in part, on the classification. CaP personalized treatment plan circuit 1853 may be configured to generate a personalized treatment plan based, at least in part, on a classification obtained from classification circuit 1757, or on a prognosis generated by prognostic circuit 1758. CaP personalized treatment plan circuit 1853 may be configured to generate a personalized treatment plan for the patient of whom the image was acquired based, at least in part, on the classification derived therefrom. Defining a personalized treatment plan facilitates delivering a particular treatment that will be therapeutically active to the patient, while minimizing negative or adverse effects experienced by the patient. For example, the personalized CaP treatment plan may suggest a surgical treatment, may suggest a pharmaceutical agent dosage or schedule, and/or other treatments. Generating a personalized treatment plan based on a more accurate prognosis of BCR or a more accurate classification of a patient as BCR low-risk or BCR high-risk facilitates more efficient delivery of costly therapeutic or surgical treatments to patients more likely to benefit from such treatments. For example, the personalized treatment plan may suggest a first surgical treatment, may suggest a first pharmaceutical agent dosage or schedule, and/or other treatments for a patient classified as a BCR low-risk, or may suggest a second, different surgical treatment or second, different pharmaceutical agent dosage or schedule or treatments for a patient classified as BCR high-risk. In this embodiment, display circuit 1759 is further configured to optionally display the personalized treatment plan.

In one embodiment of apparatus 1800, the set of circuits 1750 further includes a training and testing circuit 1851. Training and testing circuit 1851 is configured to train classification circuit 1757, or segmentation circuit 1752 on a training cohort according to various embodiments described herein. Training and testing circuit 1851 is also configured to optionally test classification circuit 1757 on a testing cohort, according to various embodiments described herein.

In one embodiment, training and testing circuit 1851 is configured to select a plurality of regions of interest (ROIs) from a set of digitized H&E stained images. Training and testing circuit 1851 is also configured to annotate a gland lumen represented in a member of the plurality of ROIs, and generate a first set of resized ROIs by resizing a member of the plurality of ROIs. Training and testing circuit 1851 is also configured to train a first deep learning model to segment a gland lumen based on the first set of resized ROIs; evaluate the first deep learning model performance; and train a final deep learning model on a second training set. In this embodiment, the second training set includes the first set of resized ROIs, and a second, different set of annotated resized ROIs, where the second, different set of annotated resized ROIs is selected based on the evaluated first deep learning model performance. Training and testing circuit 1851 is further configured to test the final deep learning model.

In one embodiment, apparatus 1800 further includes a clinical feature circuit 1855 configured to access clinical values associated with the patient. In one embodiment, clinical feature circuit 1855 is configured to access a pre-radical prostatectomy (RP) serum prostate specific antigen (PSA) level value associated with the patient. In this embodiment, clinical feature circuit 1855 is also configured to access a Gleason grade group value associated with the patient. In one embodiment, the PSA level may be defined in ng/mL. In one embodiment, the Gleason grade group value may have a value of 1, 2, 3, 4, or 5. In one embodiment, clinical feature circuit 1855 may be configured to access other, different clinical values associated with the patient, including, for example, values associated with surgical margin positivity, number of positive lymph nodes, patient age, or seminal vesicle invasion status.

In this embodiment, apparatus 1800 further includes a histotyping-plus circuit 1857. Histotyping-plus circuit 1857 is configured to compute a histotyping-plus risk score based on the histotyping risk score, the PSA level value, and the Gleason grade group value. Histotyping-plus circuit 1857 may be configured to compute the histotyping-plus risk score according to various techniques described herein. For example, histotyping-plus circuit 1857 may be configured to generate a second feature vector, where the second feature vector includes the value of the histotyping risk score, the pre-operative serum PSA level in ng/mL, and four binary variables corresponding to whether the patient was assigned Gleason grade group 2, 3, 4, or 5, respectively. In this example, histotyping-plus circuit 1857 is also configured to multiply the second feature vector by the $\beta$ values from a trained Histotyping-plus model according to techniques described herein. The nonzero elements of the $\beta$ vector correspond to Histotyping score, pre-operative PSA level, Gleason grade group 3, and Gleason grade group 4. In this example, histotyping-plus circuit 1857 is further configured to generate the histotyping-plus risk score by computing the sum of the products of the second feature vector and $\beta$ values according to various techniques described herein. In another embodiment, the nonzero elements of the $\beta$ vector may correspond to other, different Gleason grade groups, or other different clinical factors, including, for example, surgical margin positivity, number of positive lymph nodes, patient age, or seminal vesicle invasion status.

In this embodiment, classification circuit 1757 is further configured to generate a histotyping-plus classification of the patient as biochemical recurrence (BCR) high-risk or BCR low-risk based on the histotyping-plus risk score and a histotyping-plus risk score threshold. For example, classification circuit 1757 may be configured to generate a histotyping-plus classification of a patient having a histotyping-plus risk score greater than the histotyping-plus risk score threshold as BCR high-risk, while a patient having a histotyping-plus risk score less than or equal to the histotyping-plus risk score threshold may be classified as BCR low-risk. In one embodiment, the histotyping-plus risk score threshold has a value of 1.331. In another embodiment, the histotyping-plus risk score threshold may have another, different value. The histotyping-plus risk score threshold may be determined based, at least in part, on a range selected from within the range the histotyping-plus risk score is obtained, for example, [−1.210, 2.510], [−1.5, 3], [−0.5, 0.5], [−1, 1], or other range. For example, the histotyping-plus risk score threshold may, in one embodiment, be determined as the threshold that maximizes the hazard ratio in BCR-free survival time between histotyping-plus low-risk and histotyping-plus high-risk patients. In another embodiment, classification circuit 1757 may be configured to generate the histotyping-plus classification using another, different classification scheme.

In this embodiment, prognostic circuit 1758 is further configured to generate a histotyping-plus BCR prognosis. In this embodiment, prognostic circuit 1758 is configured to generate the histotyping-plus BCR prognosis based, at least in part, on the histotyping-plus classification. For example, prognostic circuit 1758 may be configured to generate a first histotyping-plus BCR prognosis associated with a patient classified as BCR high-risk, while prognostic circuit 1758 may be configured to generate a second, different histotyping-plus BCR prognosis for a patient classified as BCR low-risk.

In this embodiment, display circuit 1759 is further configured to display the histotyping-plus BCR prognosis, the histotyping-plus classification, or the histotyping-plus risk score, on a computer monitor, a smartphone display, a tablet display, or other displays, according to various techniques described herein.

In one embodiment, apparatus 1800 further includes personalized medicine device 1860. Apparatus 1800 may be configured to provide the histotyping risk score, the histotyping-plus BCR prognosis, the classification, a personalized CaP treatment plan, or other data to personalized medicine device 1860. Personalized medicine device 1860 may be, for example, a computer assisted diagnosis (CADx) system or other type of personalized medicine device that can be used to facilitate the prediction of BCR in CaP, to facilitate generating a prognosis of BCR, or to facilitate the classification of a patient as BCR low-risk or BCR high-risk. In one embodiment, CaP personalized treatment plan circuit 1853 can control personalized medicine device 1860 to display the histotyping risk score, the histotyping-plus BCR prognosis, the classification, the set of QH features, the digitized H&E stained image, a prognosis, a personalized treatment plan, or other data to on a computer monitor, a smartphone display, a tablet display, or other displays.

Figure 19:
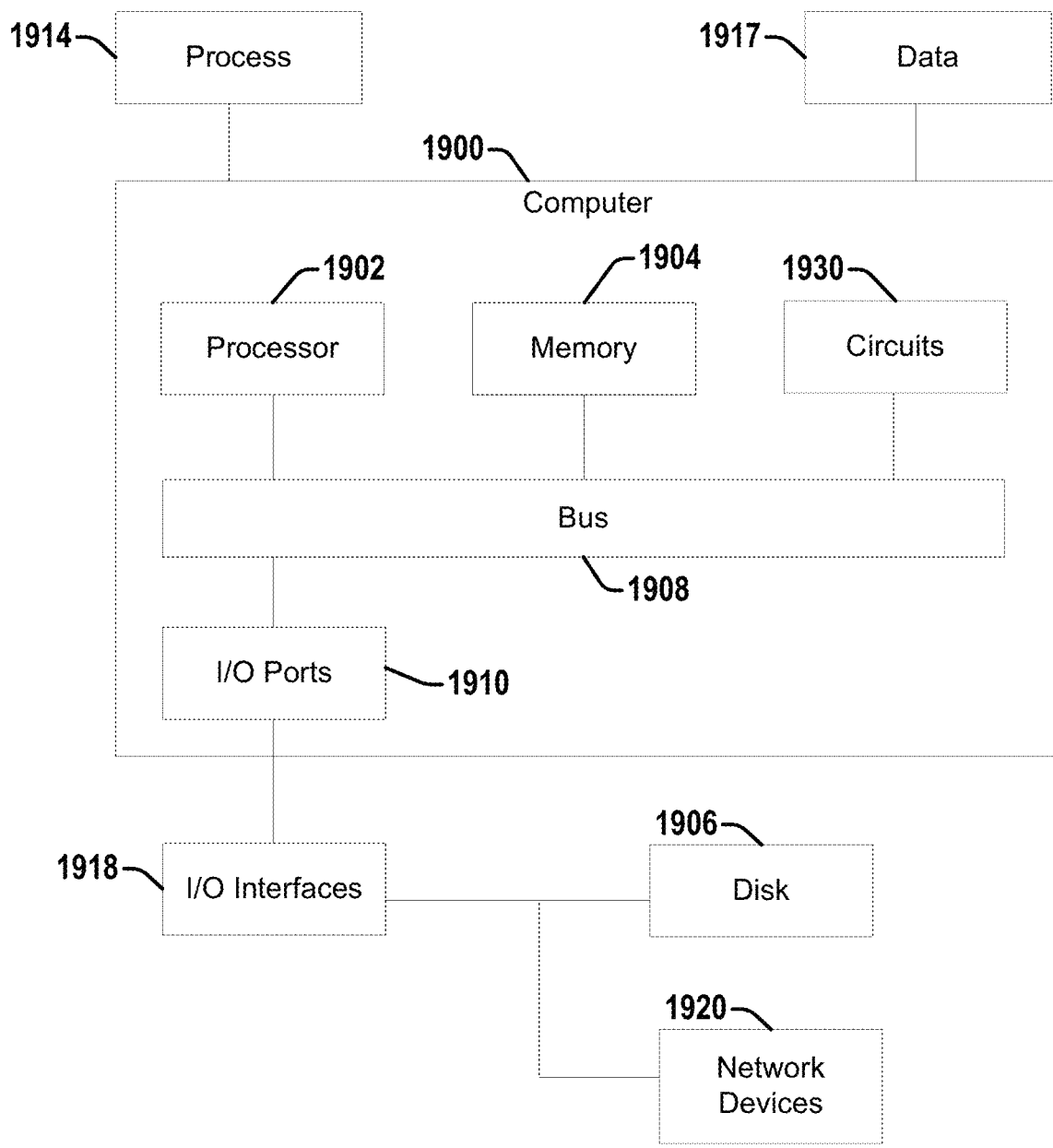
FIG. 19 illustrates a diagram of an example computer in which embodiments described herein may be implemented.

FIG. 19 illustrates an example computer 1900 in which example methods illustrated herein can operate and in which example methods, apparatus, circuits, operations, or logics may be implemented. In different examples, computer 1900 may be part of CaP BCR prediction system or apparatus, a CaP classification system or apparatus, a CaP BCR prognosis system, a CADx system, an MRI system, a CT system, a digital whole slide scanner, or a personalized medicine system, or may be operably connectable to a CaP BCR prediction system or apparatus, a CaP classification system or apparatus, a CaP BCR prognosis system, a CADx system, an MRI system, a CT system, a digital whole slide scanner, or a personalized medicine system.

Computer 1900 includes a processor 1902, a memory 1904, and input/output (I/O) ports 1910 operably connected by a bus 1908. In one example, computer 1900 may include a set of logics or circuits 1930 that perform operations for or a method of predicting BCR, generating a BCR prognosis, or classifying CaP patients as BCR low-risk or BCR high-risk based on features extracted from digitized H&E stained imagery, or further based on clinical values associated with a patient, including by using a machine learning classifier. Thus, the set of circuits 1930, whether implemented in computer 1900 as hardware, firmware, software, and/or a combination thereof may provide means (e.g., hardware, firmware, circuits) for predicting BCR in CaP, generating a BCR prognosis, or classifying CaP patients as BCR high-risk or BCR low-risk on digitized H&E stained imagery. In different examples, the set of circuits 1930 may be permanently and/or removably attached to computer 1900.

Processor 1902 can be a variety of various processors including dual microprocessor and other multi-processor architectures. Processor 1902 may be configured to perform steps of methods claimed and described herein. Memory 1904 can include volatile memory and/or non-volatile memory. A disk 1906 may be operably connected to computer 1900 via, for example, an input/output interface (e.g., card, device) 1918 and an input/output port 1910. Disk 1906 may include, but is not limited to, devices like a magnetic disk drive, a tape drive, a Zip drive, a solid state device, a flash memory card, or a memory stick. Furthermore, disk 1906 may include optical drives like a CD-ROM or a digital video ROM drive (DVD ROM). Memory 1904 can store processes 1914 or data 1917, for example. Data 1917 may, in one embodiment, include digitized H&E stained images, including images of tissue demonstrating CaP. Data 1917 may, in one embodiment, also include clinical information associated with a patient, for example, PSA levels or Gleason grade scores. Disk 1906 or memory 1904 can store an operating system that controls and allocates resources of computer 1900.

Bus 1908 can be a single internal bus interconnect architecture or other bus or mesh architectures. While a single bus is illustrated, it is to be appreciated that computer 1900 may communicate with various devices, circuits, logics, and peripherals using other buses that are not illustrated (e.g., PCIE, SATA, Infiniband, 1394, USB, Ethernet).

Computer 1900 may interact with input/output devices via I/O interfaces 1918 and input/output ports 1910. Input/output devices can include, but are not limited to, MRI systems, CT systems, digital whole slide scanners, an optical microscope, a keyboard, a microphone, a pointing and selection device, cameras, video cards, displays, disk 1906, network devices 1920, or other devices. Input/output ports 1910 can include but are not limited to, serial ports, parallel ports, or USB ports.

Computer 1900 may operate in a network environment and thus may be connected to network devices 1920 via I/O interfaces 1918 or I/O ports 1910. Through the network devices 1920, computer 1900 may interact with a network. Through the network, computer 1900 may be logically connected to remote computers. The networks with which computer 1900 may interact include, but are not limited to, a local area network (LAN), a wide area network (WAN), or other networks, including the cloud.

Figure 20:
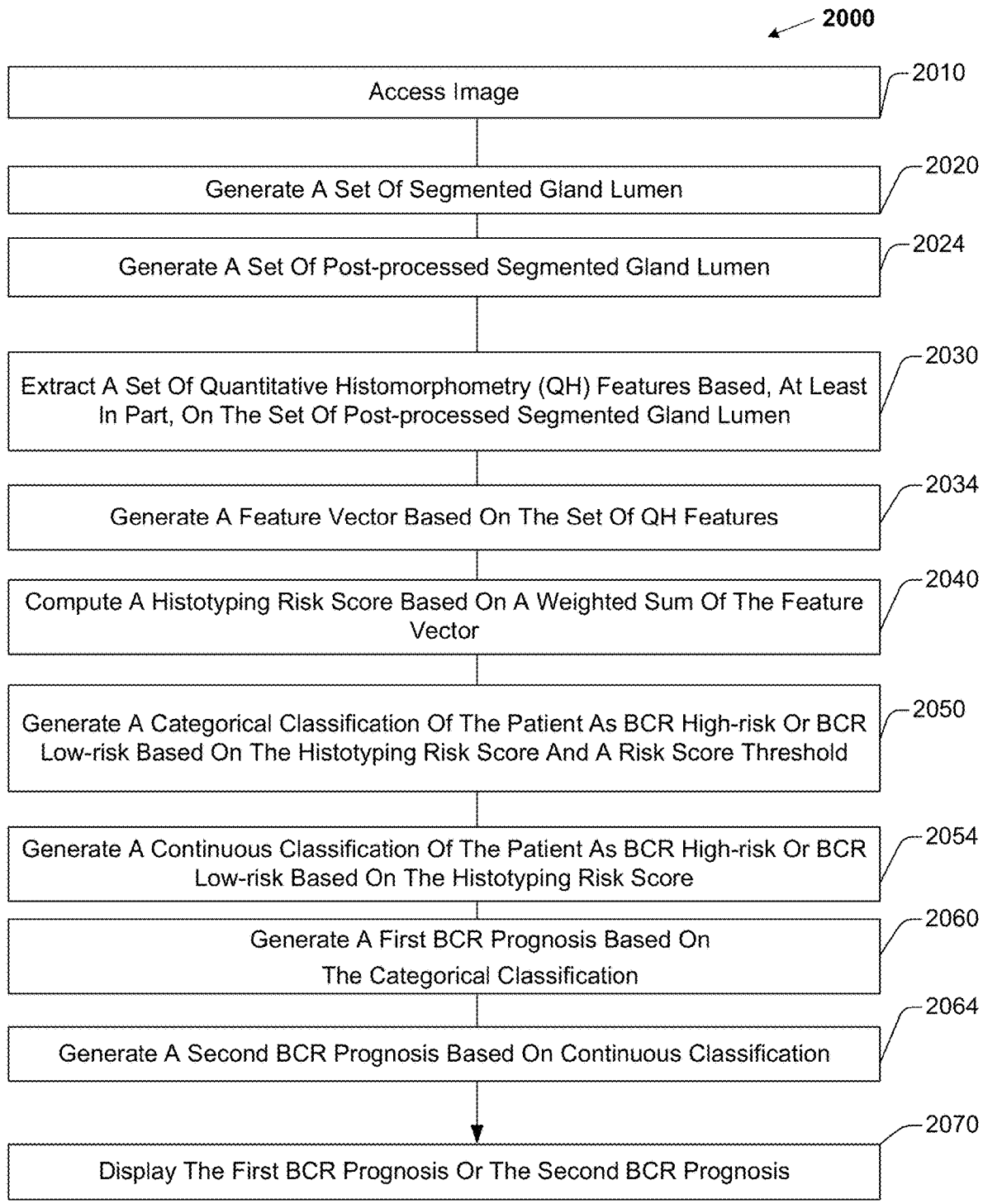
FIG. 20 illustrates a workflow diagram of an example set of operations according to various embodiments discussed herein.

FIG. 20 illustrates a method or set of operations 2000 for generating a biochemical recurrence (BCR) prognosis associated with a patient demonstrating prostate cancer (CaP) pathology. Operations 2000 includes acquiring electronic data, reading from a computer file, receiving a computer file, reading from a computer memory, or other computerized activity not practically performed in the human mind. Operations 2000 includes, at 2010, accessing a digitized hematoxylin and eosin (H&E) stained image of a region of tissue demonstrating CaP pathology. In one embodiment, the region of tissue includes an annotated tumor region, where the digitized H&E stained image includes a plurality of pixels, a pixel having an intensity, and where the digitized H&E stained image is associated with a patient.

Operations 2000 also includes, at 2020, generating a set of segmented gland lumen by segmenting a plurality of gland lumen represented in the tumor region using a deep learning segmentation model. The deep learning segmentation model may be trained to segment gland lumen on a first training set and further trained on a second training set that comprises the first training set and a second, different set of images, according to various techniques described herein.

Operations 2000 also includes, at 2024, generating a set of post-processed segmented gland lumen by re-labelling mis-labelled areas of a member of the set of segmented gland lumen, and by removing artifacts from the set of segmented gland lumen. The set of post-processed segmented gland lumen may be generated according to various techniques described herein, including, for example, operations 400.

Operations 2000 also includes, at 2030, extracting a set of quantitative histomorphometry (QH) features based, at least in part, on the set of post-processed segmented gland lumen. In one embodiment, the set of QH features includes a set of gland lumen features, a set of sub-graph features, and a set of texture features. In this embodiment, the set of gland lumen features is based, at least in part, on the post-processed set of segmented gland lumen. In this embodiment, the set of texture features includes at least one texture feature extracted from the tumor region. In this embodiment, the set of sub-graph features includes at least one sub-graph feature extracted from the tumor region. In one embodiment, the set of QH features includes at least seven gland lumen shape features, at least one sub-graph feature, and at least one Haralick feature. In one embodiment, the set of QH features includes a mean invariant moment 2 feature, a mean Fourier descriptor 4 feature, a standard deviation of smoothness feature, a median distance ratio feature, a 5%/95% perimeter ratio feature, a 5%/95% Fourier descriptor 1 feature, a 5%/95% Fourier descriptor 6 feature, a skewness of edge length sub-graph feature, and a Haralick mean correlation feature. In another embodiment, another, different number of QH features may be extracted, or the set of QH features may include other, different QH features.

Operations 2000 also includes, at 2034, generating a feature vector based on the set of QH features. In one embodiment, generating the feature vector includes normalizing the feature vector according to various techniques described herein. In one embodiment, the feature vector includes nine (9) elements.

Operations 2000 also includes, at 2040, computing a histotyping risk score based on a weighted sum of the feature vector. The histotyping risk score may be computed based on a weighted sum of the feature vector according to various techniques described herein. For example, the histotyping risk score may be computed by summing the products of the feature vector or normalized feature vector and corresponding β values according to various techniques described herein.

Operations 2000 also includes, at 2050, generating a categorical classification of the patient as BCR high-risk or BCR low-risk based on the histotyping risk score and a risk score threshold. For example, a patient associated with a histotyping risk score less than the risk score threshold may be classified as BCR low-risk, while a patient associated with a histotyping risk score greater than or equal to the risk score threshold may be classified as BCR high-risk. In one embodiment, the histotyping risk score is within the range [−0.72, 0.46], and the risk score threshold is 0.0960. In another embodiment, other ranges or risk score thresholds may be employed.

Operations 2000 also includes, at 2054, generating a continuous classification of the patient based on the histotyping risk score. For example, a patient may be classified as more or less likely to experience BCR if they are associated with a higher or lower histotyping risk score, respectively.

Operations 2000 also includes, at 2060, generating a first BCR prognosis based on the categorical classification. For example, in one embodiment, a first BCR prognosis comprising a first range of survival may be generated based on a categorical classification of BCR high-risk, while a first BCR prognosis comprising a second, different range of survival may be generated based on a categorical classification of BCR low-risk.

Operations 2000 also includes, at 2064, generating a second BCR prognosis based on the continuous classification. For example, in one embodiment, a second BCR prognosis comprising a first range of survival may be generated based on a continuous classification associated with a lower histotyping risk score, while a second BCR prognosis comprising a second, different range of survival may be generated based on a continuous classification associated with a higher histotyping risk score.

Operations 2000 further includes, at 2070, displaying the first BCR prognosis or the second BCR prognosis. Displaying the first BCR prognosis or the second BCR prognosis may include displaying the first BCR prognosis or the second BCR prognosis on a computer monitor, a smartphone display, a tablet display, or other displays. Displaying the first BCR prognosis or the second BCR prognosis may also include printing the first BCR prognosis or the second BCR prognosis.

Figure 22:
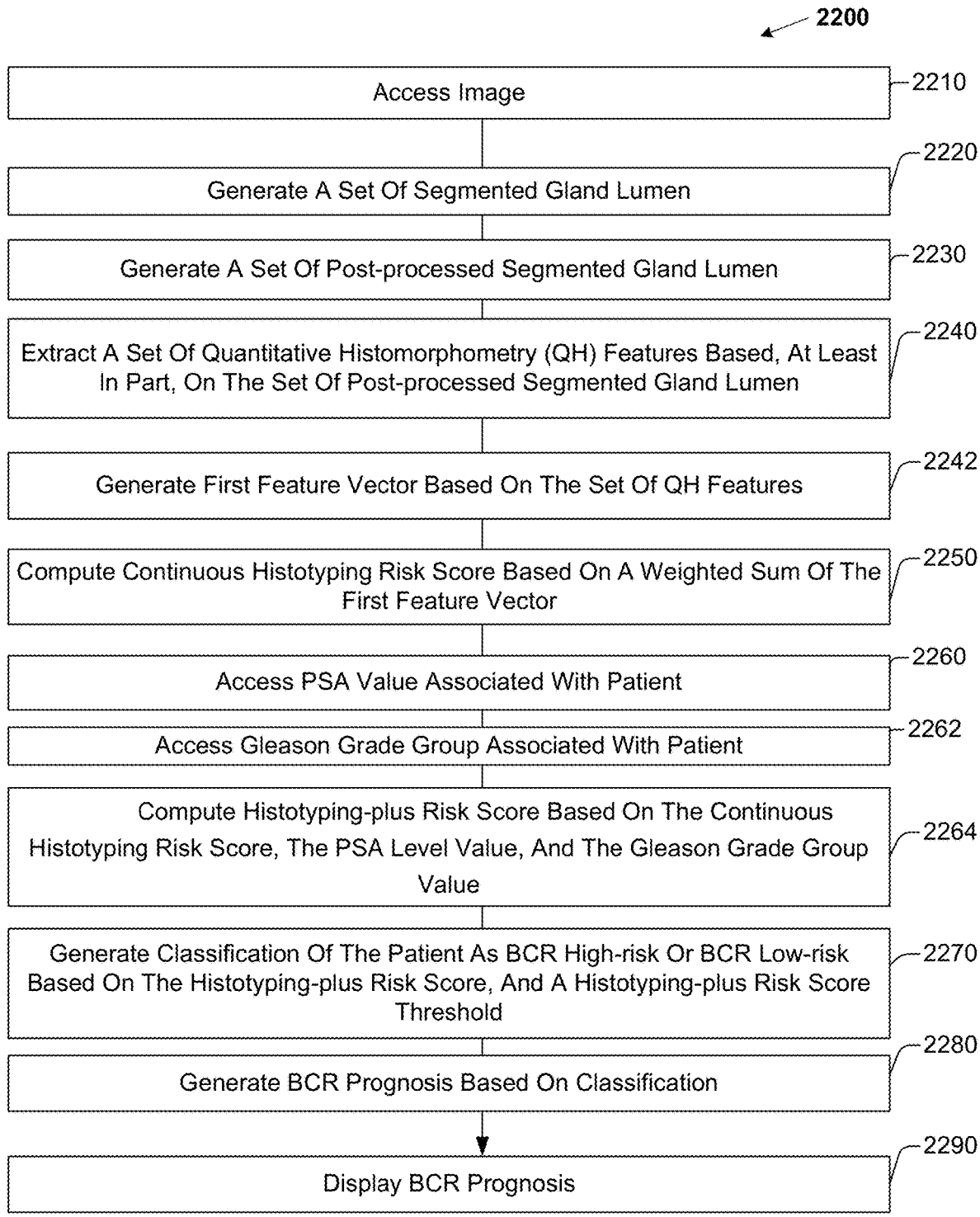
FIG. 22 illustrates a workflow diagram of an example set of operations according to various embodiments discussed herein.

In one embodiment, a non-transitory computer-readable storage device is configured to store instructions that when executed control a processor to perform operations that facilitate generating a prognosis of BCR associated with a patient. FIG. 22 illustrates an example set of operations 2200. Operations 2200 includes, at 2210 accessing a digitized image of a region of tissue demonstrating prostate cancer (CaP) pathology, where the region of tissue includes a tumor region, where the digitized image includes a plurality of pixels, a pixel having an intensity. In one embodiment, the digitized image is a digitized image of a hematoxylin and eosin (H&E) stained whole slide image (WSI) acquired post-radical prostatectomy (RP). The digitized image is associated with a patient. In one embodiment, the digitized image includes an annotated tumor region. In another embodiment, the operations 2200 further comprise automatically annotating the tumor region. Operations 2200 includes acquiring electronic data, reading from a computer file, receiving a computer file, reading from a computer memory, or other computerized activity not practically performed in the human mind.

Operations 2200 also includes, at 2220, generating a set of segmented gland lumen by segmenting a plurality of gland lumen represented in the tumor region using a deep learning segmentation model. In one embodiment, the deep learning segmentation model is trained to segment gland lumen represented in H&E stained imagery. In this embodiment, training the deep learning segmentation model includes: selecting a plurality of ROIs from a set of digitized H&E stained images; annotating a gland lumen represented in a member of the plurality of ROIs; generating a first set of resized ROIs by resizing a member of the plurality of ROIs; training a first deep learning model to segment a gland lumen based on the first set of resized ROIs; evaluating the first deep learning model performance; training a final deep learning model on a second training set, where the second training set includes the first set of resized ROIs, and a second, different set of annotated resized ROIs, where the second, different set of annotated resized ROIs is selected based on the evaluated first deep learning model performance; and testing the final deep learning model.

Operations 2200 also includes, at 2230, generating a set of post-processed segmented gland lumen by post-processing the set of segmented gland lumen. In one embodiment, post-processing the set of segmented gland lumen comprises: defining a set of post-processed segmented gland lumen, where the set of post-processed segmented gland lumen includes the members of the set of segmented gland lumen; determining if a member of the set of post-processed segmented gland lumen includes a non-lumen region; upon determining that the member of the set of post-processed segmented gland lumen includes a non-lumen region: re-labelling the non-lumen region as lumen. In this embodiment, post-processing the set of segmented gland lumen also comprises determining an area of a member of the set of segmented gland lumen; upon determining that the member of the set of segmented gland lumen has an area less than a threshold area: removing the member of the set of segmented gland lumen from the set of post-processed segmented gland lumen. In one embodiment, the threshold area is 4 $\mu m^2$. In this embodiment, post-processing the set of segmented gland lumen further comprises determining a boundary of a member of the set of segmented gland lumen; upon determining that the boundary of the member of the set of segmented gland lumen is defined by a white pixel: removing the segmented gland lumen from the set of post-processed segmented gland lumen. In one embodiment, determining that the boundary of the member of the set of segmented gland lumen is defined by a white pixel includes determining if more than a threshold percentage of pixels, for example, 5% of the pixels in the dilated boundary, are white. In another embodiment, other threshold levels, for example, 2%, or 10%, may be employed.

Operations 2200 also includes, at 2240, extracting a set of quantitative histomorphometry (QH) features from the digitized image based, at least in part, on the set of post-processed segmented gland lumen. In one embodiment, the set of QH features includes a mean invariant moment 2 feature, a mean Fourier descriptor 4 feature, a standard deviation of smoothness feature, a median distance ratio feature, a $5^{th}$ percentile/$95^{th}$ percentile perimeter ratio feature, a $5^{th}$ percentile/$95^{th}$ percentile Fourier descriptor 1 feature, a $5^{th}$ percentile/$95^{th}$ percentile Fourier descriptor 6 feature, a skewness of edge length sub-graph feature, and a Haralick mean correlation feature. In one embodiment, the set of QH features includes nine (9) QH features. In another embodiment, the set of QH features may include another, different number of features.

Operations 2200 also includes, at 2242, generating a first feature vector based on the set of QH features. In one embodiment, generating the first feature vector includes normalizing the first feature vector according to various techniques described herein.

Operations 2200 also includes, at, 2250, computing a continuous histotyping risk score based on a weighted sum of the first feature vector. In one embodiment, the continuous histotyping risk score is an unbounded value. In another embodiment, the continuous histotyping risk score is within a range, for example [−1, 1], [−0.76 to 0.42], or other range.

Operations 2200 also includes, at 2260, accessing a pre-radical prostatectomy (RP) serum prostate specific antigen (PSA) level value associated with the patient. In one embodiment, the PSA level is measured in ng/mL.

Operations 2200 also includes, at 2262, accessing a Gleason grade value associated with the patient. In one embodiment, the Gleason grade value is one of Gleason grade group 1, 2, 3, 4, or 5.

Operations 2200 also includes, at 2264, computing a histotyping-plus risk score based on the continuous histotyping risk score, the PSA level value, and the Gleason grade value. In one embodiment, computing the histotyping-plus risk score includes generating a second feature vector, where the second feature vector includes the value of the histotyping risk score, the pre-operative serum PSA level in ng/mL, and four binary variables corresponding to whether the patient was assigned Gleason grade group 2, 3, 4, or 5, respectively. The second feature vector is multiplied by the β values from a trained Histotyping-plus model according to techniques described herein. In one embodiment, the non-zero elements of the β vector correspond to Histotyping score, pre-operative PSA level, Gleason grade group 3, and Gleason grade group 4. The sum of the products of the feature vector and β values is the Histotyping-plus risk score.

Operations 2200 also includes, at 2270, generating a classification of the patient as biochemical recurrence (BCR) high-risk or BCR low-risk based on the histotyping-plus risk score, and a histotyping-plus risk score threshold. In one embodiment, the histotyping-plus risk score threshold has a value of 1.331. In another embodiment, another, different histotyping-plus risk score threshold may be employed. In another embodiment, another, different classification scheme may be employed.

Operations 2200 also includes, at 2280, generating a BCR prognosis based, at least in part, on the classification. In one embodiment, for example, a first BCR prognosis comprising a first range of survival may be generated for a patient classified as BCR high-risk, while a second, different BCR prognosis comprising a second, different range of survival may be generated for a patient classified as BCR low-risk.

Operations 2200 further includes, at 2290, displaying the BCR prognosis. Displaying the BCR prognosis may include displaying the BCR prognosis on a computer monitor, a smartphone display, a tablet display, or other displays. In one embodiment, displaying the BCR prognosis may further include optionally displaying the classification, the histotyping-plus risk score, the continuous histotyping risk score, the PSA level value, the Gleason grade value, the set of QH features, the set of post-processed segmented gland lumen, the set of segmented gland lumen, or the digitized image.

In one embodiment, operations 2200 may further include generating a personalized CaP treatment plan based on at least one of the BCR prognosis, the classification, or the histotyping-plus risk score; and optionally displaying the personalized CaP treatment plan. Operations 2200 may further include displaying the CaP treatment plan on a computer monitor, a smartphone display, a tablet display, or other displays according to various techniques described herein.

Examples herein can include subject matter such as an apparatus, a digital whole slide scanner, an MRI system, a CT system, an optical microscopy system, a personalized medicine system, a CADx system, a processor, a system, circuitry, operations, a method, means for performing operations, acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for classifying a patient as low-risk or as high-risk of BCR in CaP, or generating a BCR prognosis, according to embodiments and examples described.

Example 1 is a non-transitory computer-readable storage device storing computer-executable instructions that when executed cause a processor to perform operations, the operations comprising: accessing a digitized image of a region of tissue demonstrating prostate cancer (CaP) pathology, where the region of tissue includes a tumor region, where the digitized image includes a plurality of pixels, a pixel having an intensity, and where the digitized image is associated with a patient; generating a set of segmented gland lumen by segmenting a plurality of gland lumen represented in the tumor region using a deep learning segmentation model; generating a set of post-processed segmented gland lumen by post-processing the set of segmented gland lumen; extracting a set of quantitative histomorphometry (QH) features from the digitized image based, at least in part, on the set of post-processed segmented gland lumen; generating a feature vector based on the set of QH features; computing a histotyping risk score based on a weighted sum of the feature vector; generating a classification of the patient as biochemical recurrence (BCR) high-risk or BCR low-risk based on the histotyping risk score and a risk score threshold; generating a BCR prognosis based, at least in part, on the classification; and displaying the BCR prognosis.

Example 2 comprises the subject matter of any variation of any of example(s) 1, where the digitized image is a digitized image of a hematoxylin and eosin (H&E) stained tissue slide of a region of tissue demonstrating CaP pathology.

Example 3 comprises the subject matter of any variation of any of example(s) 1-2, where the digitized image includes an annotated tumor region.

Example 4 comprises the subject matter of any variation of any of example(s) 1-3, the operations further comprising automatically annotating the tumor region.

Example 5 comprises the subject matter of any variation of any of example(s) 1-4, where generating the post-processed set of segmented gland lumen by post-processing the set of segmented gland lumen comprises: defining a set of post-processed segmented gland lumen, where the set of post-processed segmented gland lumen includes the members of the set of segmented gland lumen; determining if a member of the set of post-processed segmented gland lumen includes a non-lumen region; upon determining that the member of the set of post-processed segmented gland lumen includes a non-lumen region: re-labelling the non-lumen region as lumen; determining an area of a member of the set of segmented gland lumen; upon determining that the member of the set of segmented gland lumen has an area less than a threshold area: removing the member of the set of segmented gland lumen from the set of post-processed segmented gland lumen; and determining a boundary of a member of the set of segmented gland lumen; upon determining that the boundary of the member of the set of segmented gland lumen is defined by a white pixel: removing the segmented gland lumen from the set of post-processed segmented gland lumen.

Example 6 comprises the subject matter of any variation of any of example(s) 1-5, where the threshold area is 4 $\mu m^2$.

Example 7 comprises the subject matter of any variation of any of example(s) 1-6, where the set of QH features includes a set of gland lumen shape features, a set of sub-graph features, and a set of texture features.

Example 8 comprises the subject matter of any variation of any of example(s) 1-7, where the set of gland lumen shape features is based, at least in part, on the post-processed set of segmented gland lumen, where the set of gland lumen shape features includes at least seven gland lumen shape features; where the set of sub-graph features includes at least one sub-graph feature based on the set of segmented gland lumen; and where the set of texture features includes at least one texture feature extracted from the tumor region.

Example 9 comprises the subject matter of any variation of any of example(s) 1-8, where the set of gland lumen shape features includes: a mean invariant moment 2 feature, a mean Fourier descriptor 4 feature, a standard deviation of smoothness feature, a median distance ratio feature, a $5^{th}$ percentile/$95^{th}$ percentile perimeter ratio feature, a $5^{th}$ percentile/$95^{th}$ percentile Fourier descriptor 1 feature, a $5^{th}$ percentile/$95^{th}$ percentile Fourier descriptor 6 feature; where the set of sub-graph features includes a skewness of edge length sub-graph feature; and where the set of texture features includes a Haralick mean correlation feature.

Example 10 comprises the subject matter of any variation of any of example(s) 1-9, where segmenting a gland lumen using a deep learning segmentation model includes segmenting a gland lumen using a deep learning model trained to segment gland lumen represented in a digitized hematoxylin and eosin (H&E) stained image of a region of tissue demonstrating CaP.

Example 11 comprises the subject matter of any variation of any of example(s) 1-10, where training the deep learning model comprises: selecting a plurality of regions of interest (ROIs) from a set of digitized H&E stained images; annotating a gland lumen represented in a member of the plurality of ROIs; generating a first set of resized ROIs by resizing a member of the plurality of ROIs; training a first deep learning model to segment a gland lumen based on the first set of resized ROIs; evaluating the first deep learning model performance; training a final deep learning model on a second training set, where the second training set includes the first set of resized ROIs, and a second, different set of annotated resized ROIs, where the second, different set of annotated resized ROIs is selected based on the evaluated first deep learning model performance; and testing the final deep learning model.

Example 12 comprises the subject matter of any variation of any of example(s) 1-11, where generating the set of resized ROIs comprises resizing a member of the plurality of ROIs to one μm per pixel.

Example 13 comprises the subject matter of any variation of any of example(s) 1-12, the operations further comprising: generating a second BCR prognosis based, at least in part, on the histotyping risk score; and displaying the second BCR prognosis.

Example 14 comprises the subject matter of any variation of any of example(s) 1-13, the operations further comprising generating a personalized CaP treatment plan based on at least one of the BCR prognosis, the second BCR prognosis, the classification, or the histotyping risk score; and optionally displaying the personalized CaP treatment plan.

Example 15 comprises the subject matter of any variation of any of example(s) 1-14, the operations further comprising: accessing a pre-radical prostatectomy (RP) serum prostate specific antigen (PSA) level value associated with the patient; accessing a Gleason grade group value associated with the patient; computing a histotyping-plus risk score based on the histotyping risk score, the PSA level value, and the Gleason grade group value; generating a second classification of the patient as biochemical recurrence (BCR) high-risk or BCR low-risk based on the histotyping-plus risk score, and a histotyping-plus risk score threshold; generating a histotyping-plus BCR prognosis based, at least in part, on the classification; and displaying the histotyping-plus BCR prognosis.

Example 16 comprises an apparatus comprising: a processor; a memory configured to store a digitized image of a region of tissue demonstrating prostate cancer (CaP) pathology; an input/output (I/O) interface; a set of circuits; and an interface that connects the processor, the memory, the I/O interface, and the set of circuits, the set of circuits comprising: an image acquisition circuit configured to acquire a digitized hematoxylin and eosin (H&E) stained image of a region of tissue demonstrating CaP pathology, where the region of tissue includes a tumor region, where the region of tissue includes a plurality of gland lumen, where the digitized H&E stained image includes a plurality of pixels, a pixel having an intensity, and where the digitized H&E stained image is associated with a patient; a segmentation circuit configured to generate a set of segmented gland lumen based on the digitized H&E stained image, where the segmentation circuit comprises a deep learning segmentation model trained to segment gland lumen represented in a digitized H&E stained image of a region of tissue demonstrating CaP; a post-processing circuit configured to generate a set of post-processed segmented gland lumen by post-processing the set of segmented gland lumen; a quantitative histomorphometry (QH) circuit configured to: extract a set of QH features based, at least in part, on the set of post-processed segmented gland lumen; and generate a feature vector based on the set of QH features; a histotyping risk score circuit configured to: compute a weighted sum of the feature vector; and compute a histotyping risk score based on the weighted sum of the feature vector; a classification circuit configured to generate a classification of the patient as biochemical recurrence (BCR) high-risk or BCR low-risk based on the histotyping risk score and a risk score threshold; a prognostic circuit configured to generate a first BCR prognosis based, at least in part, on the classification, and a second BCR prognosis based on the histotyping risk score; and a display circuit configured to display at least one of the first BCR prognosis, the second BCR prognosis, the classification, the histotyping risk score, the weighted sum of the feature vector, the feature vector, the set of QH features, the set of post-processed segmented gland lumen, or the digitized image.

Example 17 comprises the subject matter of any variation of any of example(s) 16, where the post-processing circuit is configured to: define a set of post-processed segmented gland lumen, where the set of post-processed segmented gland lumen includes the members of the set of segmented gland lumen; determine if a member of the set of post-processed segmented gland lumen includes a non-lumen region; upon determining that the member of the set of post-processed segmented gland lumen includes a non-lumen region: re-label the non-lumen region as lumen; determine an area of a member of the set of segmented gland lumen; upon determining that the member of the set of segmented gland lumen has an area less than a threshold area: remove the member of the set of segmented gland lumen from the set of post-processed segmented gland lumen; and determine a boundary of a member of the set of segmented gland lumen; upon determining that the boundary of the member of the set of segmented gland lumen is defined by a white pixel: remove the segmented gland lumen from the set of post-processed segmented gland lumen.

Example 18 comprises the subject matter of any variation of any of example(s) 16-17, the set of circuits further comprising a training circuit configured to: select a plurality of regions of interest (ROIs) from a set of digitized H&E stained images; annotate a gland lumen represented in a member of the plurality of ROIs; generate a first set of resized ROIs by resizing a member of the plurality of ROIs; train a first deep learning model to segment a gland lumen based on the first set of resized ROIs; evaluate the first deep learning model performance; train a final deep learning model on a second training set, where the second training set includes the first set of resized ROIs, and a second, different set of annotated resized ROIs, where the second, different set of annotated resized ROIs is selected based on the evaluated first deep learning model performance; and test the final deep learning model.

Example 19 comprises the subject matter of any variation of any of example(s) 16-18, where the classification circuit is further configured to generate a second BCR prognosis based, at least in part, on the histotyping risk score; and where the display circuit is further configured to display the second BCR prognosis.

Example 20 comprises the subject matter of any variation of any of example(s) 16-19, the set of circuits further comprising: a clinical feature circuit configured to: access a pre-radical prostatectomy (RP) serum prostate specific antigen (PSA) level value associated with the patient; and access a Gleason grade group value associated with the patient; and a histotyping-plus circuit configured to: compute a histotyping-plus risk score based on the histotyping risk score, the PSA level value, and the Gleason grade group value; where the classification circuit is further configured to generate a histotyping-plus classification of the patient as biochemical recurrence (BCR) high-risk or BCR low-risk based on the histotyping-plus risk score and a histotyping-plus risk score threshold; where the prognostic circuit is further configured to generate a histotyping-plus BCR prognosis based, at least in part, on the histotyping-plus classification; and where the display circuit is further configured to display the histotyping-plus BCR prognosis, the histotyping-plus classification, or the histotyping-plus risk score.

Example 21 comprises a non-transitory computer-readable storage device storing computer-executable instructions that when executed cause a processor to perform operations for generating a biochemical recurrence prognosis associated with a patient demonstrating prostate cancer (CaP) pathology, the operations comprising: accessing a digitized hematoxylin and eosin (H&E) stained image of a region of tissue demonstrating CaP pathology, where the region of tissue includes an annotated tumor region, where the digitized H&E stained image includes a plurality of pixels, a pixel having an intensity, and where the digitized H&E stained image is associated with a patient; generating a set of segmented gland lumen by segmenting a plurality of gland lumen represented in the tumor region using a deep learning segmentation model trained to segment gland lumen on a first training set, and further trained on a second training set that comprises the first training set and a second, different set of images; generating a set of post-processed segmented gland lumen by re-labelling mis-labelled areas of a member of the set of segmented gland lumen, and by removing artifacts from the set of segmented gland lumen; extracting a set of quantitative histomorphometry (QH) features based, at least in part, on the set of post-processed segmented gland lumen, where the set of QH features includes a set of gland lumen features and a set of texture features, where the set of gland lumen features includes at least two lumen arrangement features, at least one lumen orientation disorder feature, and at least ten lumen shape features, and where the set of texture features includes at least two texture features extracted from the tumor region; generating a feature vector based on the set of QH features; computing a histotyping risk score based on a weighted sum of the feature vector; generating a categorical classification of the patient as biochemical recurrence (BCR) high-risk or BCR low-risk based on the histotyping risk score and a risk score threshold; generating a continuous classification of the patient as BCR high-risk or BCR low-risk based on the histotyping risk score; generating a first BCR prognosis based on the categorical classification; generating a second BCR prognosis based on continuous classification; and displaying the first BCR prognosis or the second BCR prognosis.

Example 22 comprises a non-transitory computer-readable storage device storing computer-executable instructions that when executed cause a processor to perform operations, the operations comprising: accessing a digitized image of a region of tissue demonstrating prostate cancer (CaP) pathology, where the region of tissue includes a tumor region, where the digitized image includes a plurality of pixels, a pixel having an intensity, where the digitized image is a digitized image of a hematoxylin and eosin (H&E) stained whole slide image (WSI) acquired post-radical prostatectomy (RP), and where the digitized image is associated with a patient; generating a set of segmented gland lumen by segmenting a plurality of gland lumen represented in the tumor region using a deep learning segmentation model; generating a set of post-processed segmented gland lumen by post-processing the set of segmented gland lumen; extracting a set of quantitative histomorphometry (QH) features from the digitized image based, at least in part, on the set of post-processed segmented gland lumen; generating a first feature vector based on the set of QH features; computing a continuous histotyping risk score based on a weighted sum of the first feature vector; accessing a pre-RP serum prostate specific antigen (PSA) level value associated with the patient; accessing a Gleason grade group value associated with the patient; computing a histotyping-plus risk score based on the continuous histotyping risk score, the PSA level value, and the Gleason grade group value; generating a classification of the patient as biochemical recurrence (BCR) high-risk or BCR low-risk based on the histotyping-plus risk score, and a histotyping-plus risk score threshold; generating a BCR prognosis based, at least in part, on the classification; and displaying the BCR prognosis.

Example 23 comprises the subject matter of any variation of any of example(s) 22, where the digitized image includes an annotated tumor region.

Example 24 comprises the subject matter of any variation of any of example(s) 22-23, the operations further comprising automatically annotating the tumor region.

Example 25 comprises the subject matter of any variation of any of example(s) 22-24, where generating the post-processed set of segmented gland lumen by post-processing the set of segmented gland lumen comprises: defining a set of post-processed segmented gland lumen, where the set of post-processed segmented gland lumen includes the members of the set of segmented gland lumen; determining if a member of the set of post-processed segmented gland lumen includes a non-lumen region; upon determining that the member of the set of post-processed segmented gland lumen includes a non-lumen region: re-labelling the non-lumen region as lumen; determining an area of a member of the set of segmented gland lumen; upon determining that the member of the set of segmented gland lumen has an area less than a threshold area: removing the member of the set of segmented gland lumen from the set of post-processed segmented gland lumen; and determining a boundary of a member of the set of segmented gland lumen; upon determining that the boundary of the member of the set of segmented gland lumen is defined by a white pixel: removing the segmented gland lumen from the set of post-processed segmented gland lumen.

Example 26 comprises the subject matter of any variation of any of example(s) 22-25, where the threshold area is 4 $\mu m^2$.

Example 27 comprises the subject matter of any variation of any of example(s) 22-26, where the set of QH features includes a mean invariant moment 2 feature, a mean Fourier descriptor 4 feature, a standard deviation of smoothness feature, a median distance ratio feature, a $5^{th}$ percentile/$95^{th}$ percentile perimeter ratio feature, a $5^{th}$ percentile/$95^{th}$ percentile Fourier descriptor 1 feature, a $5^{th}$ percentile/$95^{th}$ percentile Fourier descriptor 6 feature, a skewness of edge length sub-graph feature, and a Haralick mean correlation feature.

Example 28 comprises a machine readable storage device that stores instructions for execution by a processor to perform any of the described operations of examples 1-27.

Example 29 comprises an apparatus comprising: a memory; and one or more processors configured to: perform any of the described operations of examples 1-27.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that when executed cause a processor to perform operations, the operations comprising:
    accessing a digitized image of a region of tissue demonstrating prostate cancer (CaP) pathology, where the region of tissue includes a tumor region, where the digitized image includes a plurality of pixels, a pixel having an intensity, and where the digitized image is associated with a patient;
    generating a set of segmented gland lumen by segmenting a plurality of gland lumen represented in the tumor region using a deep learning segmentation model;
    generating a set of post-processed segmented gland lumen by post-processing the set of segmented gland lumen;
    extracting a set of quantitative histomorphometry (QH) features from the digitized image based, at least in part, on the set of post-processed segmented gland lumen;
    generating a feature vector based on the set of QH features;
    computing a histotyping risk score based on a weighted sum of the feature vector;
    generating a classification of the patient as biochemical recurrence (BCR) high-risk or BCR low-risk based on the histotyping risk score and a risk score threshold;
    generating a BCR prognosis based, at least in part, on the classification; and
    displaying the BCR prognosis.

2. The non-transitory computer-readable storage device of claim 1, where the digitized image is a digitized image of a hematoxylin and eosin (H&E) stained tissue slide of the region of tissue demonstrating CaP pathology.

3. The non-transitory computer-readable storage device of claim 1, where the digitized image includes an annotated tumor region.

4. The non-transitory computer-readable storage device of claim 1, the operations further comprising automatically annotating the tumor region.

5. The non-transitory computer-readable storage device of claim 1, where generating the set of post-processed segmented gland lumen by post-processing the set of segmented gland lumen comprises:
    defining the set of post-processed segmented gland lumen, where the set of post-processed segmented gland lumen includes the members of the set of segmented gland lumen;
    determining if a member of the set of post-processed segmented gland lumen includes a non-lumen region;
    upon determining that the member of the set of post-processed segmented gland lumen includes the non-lumen region:
        re-labelling the non-lumen region as lumen;
    determining an area of a member of the set of segmented gland lumen;
    upon determining that the member of the set of segmented gland lumen has an area less than a threshold area:
        removing the member of the set of segmented gland lumen from the set of post-processed segmented gland lumen; and
    determining a boundary of a member of the set of segmented gland lumen;
    upon determining that the boundary of the member of the set of segmented gland lumen is defined by a white pixel:
        removing the segmented gland lumen from the set of post-processed segmented gland lumen.

6. The non-transitory computer-readable storage device of claim 5, where the threshold area is 4 $\mu m^2$.

7. The non-transitory computer-readable storage device of claim 1, where the set of QH features includes a set of gland lumen shape features, a set of sub-graph features, and a set of texture features.

8. The non-transitory computer-readable storage device of claim 7, where the set of gland lumen shape features is based, at least in part, on the set of post-processed segmented gland lumen, where the set of gland lumen shape features includes at least seven gland lumen shape features;
    where the set of sub-graph features includes at least one sub-graph feature based on the set of segmented gland lumen; and
    where the set of texture features includes at least one texture feature extracted from the tumor region.

9. The non-transitory computer-readable storage device of claim 8,
    where the set of gland lumen shape features includes: a mean invariant moment 2 feature, a mean Fourier descriptor 4 feature, a standard deviation of smoothness feature, a median distance ratio feature, a $5^{th}$ percentile/$95^{th}$ percentile perimeter ratio feature, a $5^{th}$ percentile/$95^{th}$ percentile Fourier descriptor 1 feature, a $5^{th}$ percentile/$95^{th}$ percentile Fourier descriptor 6 feature;
    where the set of sub-graph features includes a skewness of edge length sub-graph feature; and
    where the set of texture features includes a Haralick mean correlation feature.

10. The non-transitory computer-readable storage device of claim 1, where segmenting the plurality of gland lumen using the deep learning segmentation model includes segmenting a gland lumen using a deep learning model trained to segment gland lumen represented in a digitized hematoxylin and eosin (H&E) stained image of the region of tissue demonstrating CaP.

11. The non-transitory computer-readable storage device of claim 10, where training the deep learning model comprises:
    selecting a plurality of regions of interest (ROIs) from a set of digitized H&E stained images;
    annotating a gland lumen represented in a member of the plurality of ROIs;
    generating a first set of resized ROIs by resizing the member of the plurality of ROIs;
    training a first deep learning model to segment the gland lumen based on the first set of resized ROIs;
    evaluating the first deep learning model performance;
    training a final deep learning model on a second training set, where the second training set includes the first set of resized ROIs, and a second, different set of annotated resized ROIs, where the second, different set of annotated resized ROIs is selected based on the evaluated first deep learning model performance; and
    testing the final deep learning model.

12. The non-transitory computer-readable storage device of claim 11, where generating the first set of resized ROIs comprises resizing the member of the plurality of ROIs to one µm per pixel.

13. The non-transitory computer-readable storage device of claim 1, the operations further comprising:
    generating a second BCR prognosis based, at least in part, on the histotyping risk score; and
    displaying the second BCR prognosis.

14. The non-transitory computer-readable storage device of claim 13, the operations further comprising:
    generating a personalized CaP treatment plan based on at least one of the BCR prognosis, the second BCR prognosis, the classification, or the histotyping risk score; and
    optionally displaying the personalized CaP treatment plan.

15. The non-transitory computer-readable storage device of claim 1, the operations further comprising:
    accessing a pre-radical prostatectomy (RP) serum prostate specific antigen (PSA) level value associated with the patient;
    accessing a Gleason grade group value associated with the patient;
    computing a histotyping-plus risk score based on the histotyping risk score, the PSA level value, and the Gleason grade group value;
    generating a second classification of the patient as biochemical recurrence (BCR) high-risk or BCR low-risk based on the histotyping-plus risk score, and a histotyping-plus risk score threshold;
    generating a histotyping-plus BCR prognosis based, at least in part, on the classification; and
    displaying the histotyping-plus BCR prognosis.

16. An apparatus comprising:
    a processor;
    a memory configured to store a digitized image of a region of tissue demonstrating prostate cancer (CaP) pathology;
    an input/output (I/O) interface;
    a set of circuits; and
    an interface that connects the processor, the memory, the I/O interface, and the set of circuits, the set of circuits comprising:
        an image acquisition circuit configured to acquire a digitized hematoxylin and eosin (H&E) stained image of the region of tissue demonstrating CaP pathology, where the region of tissue includes a tumor region, where the region of tissue includes a plurality of gland lumen, where the digitized H&E stained image includes a plurality of pixels, a pixel having an intensity, and where the digitized H&E stained image is associated with a patient;
        a segmentation circuit configured to generate a set of segmented gland lumen based on the digitized H&E stained image, where the segmentation circuit comprises a deep learning segmentation model trained to segment gland lumen represented in the digitized H&E stained image of the region of tissue demonstrating CaP;
        a post-processing circuit configured to generate a set of post-processed segmented gland lumen by post-processing the set of segmented gland lumen;
        a quantitative histomorphometry (QH) circuit configured to:
            extract a set of QH features based, at least in part, on the set of post-processed segmented gland lumen; and
            generate a feature vector based on the set of QH features;
        a histotyping risk score circuit configured to:
            compute a weighted sum of the feature vector; and
            compute a histotyping risk score based on the weighted sum of the feature vector;
        a classification circuit configured to generate a classification of the patient as biochemical recurrence (BCR) high-risk or BCR low-risk based on the histotyping risk score and a risk score threshold;
        a prognostic circuit configured to generate a first BCR prognosis based, at least in part, on the classification, and a second BCR prognosis based on the histotyping risk score; and
        a display circuit configured to display at least one of the first BCR prognosis, the second BCR prognosis, the classification, the histotyping risk score, the weighted sum of the feature vector, the feature vector, the set of QH features, the set of post-processed segmented gland lumen, or the digitized image.

17. The apparatus of claim 16, where the post-processing circuit is configured to:
    define the set of post-processed segmented gland lumen, where the set of post-processed segmented gland lumen includes the members of the set of segmented gland lumen;
    determine if a member of the set of post-processed segmented gland lumen includes a non-lumen region;
    upon determining that the member of the set of post-processed segmented gland lumen includes the non-lumen region:
        re-label the non-lumen region as lumen;
    determine an area of a member of the set of segmented gland lumen;
    upon determining that the member of the set of segmented gland lumen has an area less than a threshold area:
        remove the member of the set of segmented gland lumen from the set of post-processed segmented gland lumen; and
    determine a boundary of a member of the set of segmented gland lumen;

upon determining that the boundary of the member of the set of segmented gland lumen is defined by a white pixel:
  remove the segmented gland lumen from the set of post-processed segmented gland lumen.

18. The apparatus of claim 17, the set of circuits further comprising a training circuit configured to:
  select a plurality of regions of interest (ROIs) from a set of digitized H&E stained images;
  annotate a gland lumen represented in a member of the plurality of ROIs;
  generate a first set of resized ROIs by resizing the member of the plurality of ROIs;
  train a first deep learning model to segment the gland lumen based on the first set of resized ROIs;
  evaluate the first deep learning model performance;
  train a final deep learning model on a second training set, where the second training set includes the first set of resized ROIs, and a second, different set of annotated resized ROIs, where the second, different set of annotated resized ROIs is selected based on the evaluated first deep learning model performance; and
  test the final deep learning model.

19. The apparatus of claim 16, where the classification circuit is further configured to generate the second BCR prognosis based, at least in part, on the histotyping risk score; and where the display circuit is further configured to display the second BCR prognosis.

20. The apparatus of claim 16, the set of circuits further comprising:
  a clinical feature circuit configured to:
    access a pre-radical prostatectomy (RP) serum prostate specific antigen (PSA) level value associated with the patient; and
    access a Gleason grade group value associated with the patient; and
  a histotyping-plus circuit configured to:
    compute a histotyping-plus risk score based on the histotyping risk score, the PSA level value, and the Gleason grade group value;
  where the classification circuit is further configured to generate a histotyping-plus classification of the patient as biochemical recurrence (BCR) high-risk or BCR low-risk based on the histotyping-plus risk score and a histotyping-plus risk score threshold;
  where the prognostic circuit is further configured to generate a histotyping-plus BCR prognosis based, at least in part, on the histotyping-plus classification; and
  where the display circuit is further configured to display the histotyping-plus BCR prognosis, the histotyping-plus classification, or the histotyping-plus risk score.

21. A non-transitory computer-readable storage device storing computer-executable instructions that when executed cause a processor to perform operations for generating a biochemical recurrence prognosis associated with a patient demonstrating prostate cancer (CaP) pathology, the operations comprising:
  accessing a digitized hematoxylin and eosin (H&E) stained image of a region of tissue demonstrating CaP pathology, where the region of tissue includes an annotated tumor region, where the digitized H&E stained image includes a plurality of pixels, a pixel having an intensity, and where the digitized H&E stained image is associated with a patient;
  generating a set of segmented gland lumen by segmenting a plurality of gland lumen represented in the tumor region using a deep learning segmentation model trained to segment gland lumen on a first training set, and further trained on a second training set that comprises the first training set and a second, different set of images;
  generating a set of post-processed segmented gland lumen by re-labelling mis-labelled areas of a member of the set of segmented gland lumen, and by removing artifacts from the set of segmented gland lumen;
  extracting a set of quantitative histomorphometry (QH) features based, at least in part, on the set of post-processed segmented gland lumen, where the set of QH features includes a set of gland lumen features and a set of texture features, where the set of gland lumen features includes at least two lumen arrangement features, at least one lumen orientation disorder feature, and at least ten lumen shape features, and where the set of texture features includes at least two texture features extracted from the tumor region;
  generating a feature vector based on the set of QH features;
  computing a histotyping risk score based on a weighted sum of the feature vector;
  generating a categorical classification of the patient as biochemical recurrence (BCR) high-risk or BCR low-risk based on the histotyping risk score and a risk score threshold;
  generating a continuous classification of the patient as BCR high-risk or BCR low-risk based on the histotyping risk score;
  generating a first BCR prognosis based on the categorical classification;
  generating a second BCR prognosis based on continuous classification; and
  displaying the first BCR prognosis or the second BCR prognosis.

22. A non-transitory computer-readable storage device storing computer-executable instructions that when executed cause a processor to perform operations, the operations comprising:
  accessing a digitized image of a region of tissue demonstrating prostate cancer (CaP) pathology, where the region of tissue includes a tumor region, where the digitized image includes a plurality of pixels, a pixel having an intensity, where the digitized image is a digitized image of a hematoxylin and eosin (H&E) stained whole slide image (WSI) acquired post-radical prostatectomy (RP), and where the digitized image is associated with a patient;
  generating a set of segmented gland lumen by segmenting a plurality of gland lumen represented in the tumor region using a deep learning segmentation model;
  generating a set of post-processed segmented gland lumen by post-processing the set of segmented gland lumen;
  extracting a set of quantitative histomorphometry (QH) features from the digitized image based, at least in part, on the set of post-processed segmented gland lumen;
  generating a first feature vector based on the set of QH features;
  computing a continuous histotyping risk score based on a weighted sum of the first feature vector;
  accessing a pre-RP serum prostate specific antigen (PSA) level value associated with the patient;
  accessing a Gleason grade group value associated with the patient;
  computing a histotyping-plus risk score based on the continuous histotyping risk score, the PSA level value, and the Gleason grade group value;

generating a classification of the patient as biochemical recurrence (BCR) high-risk or BCR low-risk based on the histotyping-plus risk score, and a histotyping-plus risk score threshold;

generating a BCR prognosis based, at least in part, on the classification; and displaying the BCR prognosis.

23. The non-transitory computer-readable storage device of claim 22, where the digitized image includes an annotated tumor region.

24. The non-transitory computer-readable storage device of claim 22, the operations further comprising automatically annotating the tumor region.

25. The non-transitory computer-readable storage device of claim 22, where generating the set of post-processed segmented gland lumen by post-processing the set of segmented gland lumen comprises:

defining the set of post-processed segmented gland lumen, where the set of post-processed segmented gland lumen includes the members of the set of segmented gland lumen;

determining if a member of the set of post-processed segmented gland lumen includes a non-lumen region;

upon determining that the member of the set of post-processed segmented gland lumen includes a non-lumen region:

re-labelling the non-lumen region as lumen;

determining an area of a member of the set of segmented gland lumen;

upon determining that the member of the set of segmented gland lumen has an area less than a threshold area:

removing the member of the set of segmented gland lumen from the set of post-processed segmented gland lumen; and determining a boundary of a member of the set of segmented gland lumen;

upon determining that the boundary of the member of the set of segmented gland lumen is defined by a white pixel:

removing the segmented gland lumen from the set of post-processed segmented gland lumen.

26. The non-transitory computer-readable storage device of claim 25, where the threshold area is 4 $\mu m^2$.

27. The non-transitory computer-readable storage device of claim 22, where the set of QH features includes a mean invariant moment 2 feature, a mean Fourier descriptor 4 feature, a standard deviation of smoothness feature, a median distance ratio feature, a $5^{th}$ percentile/$95^{th}$ percentile perimeter ratio feature, a $5^{th}$ percentile/$95^{th}$ percentile Fourier descriptor 1 feature, a $5^{th}$ percentile/$95^{th}$ percentile Fourier descriptor 6 feature, a skewness of edge length sub-graph feature, and a Haralick mean correlation feature.

* * * * *

UNITED STATES PATENT AND TRADEMARK OFFICE
CERTIFICATE OF CORRECTION

PATENT NO.        : 11,494,900 B2
APPLICATION NO.   : 16/729697
DATED             : November 8, 2022
INVENTOR(S)       : Anant Madabhushi et al.

Page 1 of 1

It is certified that error appears in the above-identified patent and that said Letters Patent is hereby corrected as shown below:

In the Specification

Column 1, Lines 17-26; please replace "This invention was made with government support under the grants CA199374, CA202752, CA208236, CA216579, CA220581, RR012463, CA239055, and EB028736 awarded by the National Institutes of Health; grant IBX004121A awarded by the United States Depar•tment of Veterans Affairs; grants W81XWH-19-I-0668, W81XWH-15-I-0558, W81XWH-18-l-0440, and W81XWH-16-l-0329 awarded by the United States Depart•ment of Defense; and grant DGE1451075 awarded by the National Science Foundation. The government has certain rights in the invention." With --This invention was made with government support under W81XWH-19-1-0668, W81XWH-18-1-0440, W81XWH-16-1-0329, and W81XWH-15-1-0558 awarded by the Department of Defense; CA199374, RR012463, EB028736, CA239055, CA220581, CA216579, CA208236, and CA202752 awarded by the National Institutes of Health; 1451075 awarded by the National Science Foundation; and IBX004121A awarded by Department of Veterans Affairs. The government has certain rights in the invention.--

Signed and Sealed this
Second Day of September, 2025

Coke Morgan Stewart
*Acting Director of the United States Patent and Trademark Office*